United States Patent
Matsuda et al.

(10) Patent No.: US 6,376,203 B1
(45) Date of Patent: Apr. 23, 2002

(54) GLYCOGLYCEROPHOSPHOLIPID, ANTIBODY THEREAGAINST, AND METHOD FOR DETECTING MYCOPLASMA

(75) Inventors: Kazuhiro Matsuda, Yamaguchi; Naoki Yamamoto, Tokyo, both of (JP)

(73) Assignee: Seikagaku Corporation, Tokyo (JP)

( * ) Notice: Subject to any disclaimer, the term of this patent is extended or adjusted under 35 U.S.C. 154(b) by 0 days.

(21) Appl. No.: 09/349,824

(22) Filed: Jul. 8, 1999

Related U.S. Application Data

(62) Division of application No. 08/750,677, filed on Dec. 3, 1996, now Pat. No. 5,994,090.

(30) Foreign Application Priority Data

Jun. 3, 1994 (JP) .............................................. 6-145537
Oct. 26, 1994 (JP) .............................................. 6-286038

(51) Int. Cl.[7] .......................... G01N 33/554; C12Q 1/04; A61K 39/395; A61K 39/40; C07H 5/04
(52) U.S. Cl. ................ 435/7.32; 424/130.1; 424/137.1; 424/141.1; 424/150.1; 424/163.1; 424/264.1; 435/7.1; 435/34; 536/55.1; 536/123.1
(58) Field of Search ........................... 424/130.1, 137.1, 424/141.1, 150.1, 163.1, 264.1; 435/7.1, 7.32, 34; 536/55.1, 123.1

(56) References Cited

U.S. PATENT DOCUMENTS

| | | | |
|---|---|---|---|
| 4,666,851 A | 5/1987 | Lee | 424/3 |
| 4,945,041 A | 7/1990 | Baseman | 435/7 |
| 5,158,870 A | 10/1992 | Baseman et al. | 435/7.32 |
| 5,242,820 A | 9/1993 | Shyh-Ching Lo | 425/240.2 |
| 5,332,567 A | 7/1994 | Goldenberg | 424/1.49 |

OTHER PUBLICATIONS

Kim S. Wise, et al., A Family of Strain–Variant Surface Lipoproteins of *Mycoplasma fermentans*, Infection and Immunity, Aug. 1993, p. 3327–333 vol. 61(8).

Shaw–Huey Feng, et al., Induced Mouse Spleen B–Cell proliferation and Secretion of Immunoglobulin by Lipid–Associated membrane Proteins of *Mycoplasma fermentans* Incognitus and *Mycoplasma penetrans*, Infection and Immunity, Sep. 1994, p. 3916–3921, vol. 62(9).

Kazuhiro Matsuda, et al., Identification of Phosphocholine–Containing Glycoglycerolipids Purified from *Mycoplasma fermentans*–Infected Human Helper T–Cell Culture as Components of *M. fermentans*, Microbiol, Immunol., 39(5), 307–313, 1995.

K. Matsuda, et al.: "Occurrence of a novel glycolipid containing Phosphocholine in HTLV–infected cells", J. Glycoconjugate, vol. 10 1993, p. 340.

H–G. Schiefer, et al.: "Localization of a phosphoglycolipid in Mycoplasma membranes using specific anti–lipid–antibodies" Zentralblatt fur Bakteriologie, Parasitenkunde, Infektionskrankheiten und Hygiene, vol. 239, 1977, pp. 262–269.

M. Salman, et al.: "Membrane lipids of *Mycoplasma fermentans*", FEMS Microbiol. Lett., vol. 123, 1994, pp. 255–260. 1.

K. Matsuda, et al.: "Identification of phosphocholine–containing glycoglycerolipids purified from *Mycoplasma fermentans*–infected human helper T–cell culture as components of *M. fermentans*" Microbiol, Immunol., vol. 39. No. 5, 1995 pp. 307–313.

*Primary Examiner*—Rodney P Swartz
(74) *Attorney, Agent, or Firm*—Knobbe, Martens, Olson & Bear, LLP

(57) ABSTRACT

Mouse is immunized with an antigen of a lipid fraction originating from *Mycoplasma fermentans*. Its spleen cells are fused with mouse myeloma cells to prepare hybridomas. A hybridoma is selected, which produces a monoclonal antibody having reaction specificity to GGPL-III that is a phosphocholine-containing glycoglycerolipid specific to *Mycoplasma fermentans*. *Mycoplasma fermentans* is detected by using the obtained antibody.

20 Claims, 15 Drawing Sheets

1. POLYCLONAL ANTIBODY
2. NON-IMMUNIZED MOUSE SERUM

GLYCOGLYCEROPHOSPHOLIPID, ANTIBODY THEREAGAINST, AND METHOD FOR DETECTING MYCOPLASMA

This application is a divisional of prior application Ser. No. 08/750,677, filed Dec. 3, 1996 now U.S. Pat. No. 5,994,090.

TECHNICAL FIELD

The present invention relates to a novel glycoglycerophospholipid originating from *Mycoplasma fermentans*, an antibody against the glycoglycerophospholipid specifically existing in *Mycoplasma fermentans*, a method for measuring the glycoglycerophospholipid based on the use of the antibody, and a method for detecting *Mycoplasma fermentans*.

BACKGROUND ART

The present inventors have already found five species of glycoglycerophospholipids (phosphocholine-containing glycoglycerolipids) from MT-4 cells (human helper T cells infected with HTLV-I (human T lymphotropic retrovirus Type I), Miyoshi et al., Gann., 71, 155–156 (1980)). The present inventors have previously found that one of the five species of glycoglycerophospholipids is 6'-O-phosphocholine-α-glucopyranosyl-(1'-3)-1,2-diacyl-sn-glycerol (Shishitsu-Seikagaku-Kenkyu (*Studies on Lipid Biochemistry*), Vol. 35, pp. 111–114, 1993).

On the other hand, it has been reported that *Macodlasma fermentans* is an exacerbation factor of human acquired immunodeficiency syndrome (AIDS) (Lo. S., -C. et al., 1991, *Science*, 251: 1074–1076; U.S. Pat. No. 5,242,820), or *Mycoplasma fermentans* is a cause of rheumatism (Williams, M. H. et al., 1970, *Lancet ii:* 277–280).

Various antibodies against mycoplasmas have been hitherto known, and they have been also used for clinical examination. However, the majority of them are antibodies against *Mycoplasma pneumoniae* or *Mycoplasma genitalium*. Monoclonal antibodies against these mycoplasmas have been also prepared. However, it is presumed that such an antibody is an antibody which recognizes a protein of a mycoplasma, or simultaneously recognizes a protein and a lipid of a mycoplasma. Further, any of such antibodies does not exhibit specificity to *Mycoplasma fermentans* (Japanese Patent Laid-open Nos. 63–298, 63–184064, 63–32496, and 5-304990, and U.S. Pat. Nos. 5,158,870, 4,945,041, and 5,242,820). An antibody, which exhibits specificity to *Mycoplasma fermentans*, is disclosed in U.S. Pat. No. 5,242,820. However, this antibody is obtained by using an entire extract of mycoplasmal cells as an immunogen, and thus the antibody is regarded as an antibody which recognizes a protein. Accordingly, if a mycoplasma contained in a body fluid such as a serum which contains various proteins is detected by using this antibody, the antibody highly possibly makes nonspecific binding. Therefore, it may be impossible to expect a high sensitivity. Further, when an antigen is a protein, it is sufficiently assumed that antigenicity disappears due to mutation in an amino acid sequence of the protein.

As far as the present inventors know, it has not been reported that any mycoplasma has a glycoglycerophospholipid containing phosphocholine. Further, no instance has been known, in which a glycoglycerophospholipid originating from a mycoplasma is used as an immunogen to obtain an antibody which exhibits specificity to the glycoglycerophospholipid. Moreover, it has not been known at all as well that the antibody, which exhibits the specificity to the glycoglycerophospholipid, exhibits high specificity to *Mycoplasma fementans*.

DISCLOSURE OF THE INVENTION

It has been reported that the process of pathology of a patient infected with a human immunodeficiency virus is accelerated to arrive at AIDS by infection of a mycoplasma (1991, *Science,* 251: 4991). It has been also reported that *Mycoplasma fementans* is an exacerbation factor of AIDS as described above. However, there is no means to correctly detect such behavior of *Mycoplasma fermentans* in vivo. Therefore, it has been desired to provide an antibody capable of immunologically detecting *Mycoplasma fementans* in vivo.

The present invention has been made considering a viewpoint as described above, an object of which is to elucidate a glycoglycerophospholipid specifically existing in *Mycoplasma fementans*, and provide an antibody against the glycoglycerophospholipid, a method for measuring the glycoglycerophospholipid based on the use of the antibody, and a method for detecting *Mycoplasma fementans*.

In order to elucidate abnormal proliferation of cells, destruction of cells, and immunological abnormality caused by infection with a retrovirus, the present inventors have analyzed lipids of such infected cells. During this process, the present inventors have confirmed that a glycoglycerophospholipid (phosphocholine-containing glycoglycerolipid) extracted from a human helper T cell strain is unexpectedly a glycoglycerophospholipid originating from *Mycoplasma fermentans* (phosphocholine-containing glycoglycerolipid: hereinafter simply referred to as "glycoglycerophospholipid). Further, the present inventors have elucidated a structure of the lipid. Moreover, the present inventors have prepared an antibody against the lipid, and confirmed specificity to various mycoplasmas. As a result, the present inventors have found out that the antibody specifically recognizes *Mycoplasma fementans*. Thus the present invention has been completed.

Namely, the present invention lies in a glycoglycerophospholipid extractable from *Mycoplasma fermentans*, having the following properties:

(A) the glycoglycerophospholipid is reactive with orcinol reagent, Dittmer reagent, Dragendorff reagent, and ninhydrin reagent;

(B) the glycoglycerophospholipid is degradable with alkali;

(C) the glycoglycerophospholipid is obtained as a non-adsorptive fraction upon fractionation with an anion exchanger having diethylaminoethyl group; and (D) the glycoglycerophospholipid has a molecular weight of 1048+28n measured by using a mass spectrometer, wherein n is −1, 0, 1, or 2.

The glycoglycerophospholipid described above highly possibly comprises constitutional components of α-glucopyranosyl-(1'-3)-1,2-diacyl-sn-glycerol, phosphocholine, and phosphoric ester of aminopropanediol.

In another aspect, the present invention lies in an anti-glycoglycerophospholipid antibody having reaction specificity to a glycoglycerophospholipid comprising at least phosphocholine, glucose, fatty acid, and glycerol, the lipid being non-adsorptive to an anion exchanger having diethylaminoethyl group, and unstable against alkali. The glycoglycerophospholipid includes, for example, a glycoglycerophospholipid specifically existing in *Mycoplasma fementans*.

The present invention provides, as specified embodiments of the anti-glycoglycerophospholipid antibody, an anti-glycoglycerophospholipid polyclonal antibody which reacts with both of 6'-O-phosphocholine -α-glucopyranosyl-(1'-3)-1,2-diacyl-sn-glycerol and the glycoglycerophospholipid extractable from *Mycoplasma fermentans*, having the following properties, and an anti-glycoglycerophospholipid monoclonal antibody which has reaction specificity to the glycoglycerophospholipid having the following properties:

(A) the glycoglycerophospholipid is reactive with orcinol reagent, Dittmer reagent, Dragendorff reagent, and ninhydrin reagent;

(B) the glycoglycerophospholipid is degradable with alkali;

(C) the glycoglycerophospholipid is obtained as a non-adsorptive fraction upon fractionation with an anion exchanger having diethylaminoethyl group; and (D) the glycoglycerophospholipid has a molecular weight of 1048+28n measured by using a mass spectrometer, wherein n is −1, 0, 1, or 2.

In further aspects, the present invention provides a method for measuring a glycoglycerophospholipid, comprising the step of immunologically measuring the glycoglycerophospholipid having the foregoing properties contained in a specimen, by using the foregoing anti-glycoglycerophospholipid antibody, and a method for detecting *Mycoplasma fementans*, comprising the steps of measuring a glycoglycerophospholipid contained in a specimen in accordance with the foregoing method, and relating the presence or absence of the glycoglycerophospholipid or an existing amount thereof to the presence or absence of *Mycoplasma fementans* or an existing amount thereof in the specimen.

In still another aspect, the present invention provides a method for measuring the glycoglycerophospholipid having the foregoing properties (A) to (D) and/or a substance having antigenicity similar to that of the glycoglycerophospholipid contained in a specimen, comprising the step of immunologically measuring the glycoglycerophospholipid and/or the substance having the antigenicity similar to that of the glycoglycerophospholipid by using the foregoing anti-glycoglycerophospholipid antibody.

In still another aspect, the present invention provides a reagent kit for detecting *Myconlasma fermentans* or a glycoglycerophospholipid of *Mycoplasma fermentans* contained in a specimen in accordance with an immunological method, comprising the foregoing anti-glycoglycerophospholipid antibody, and a glycoglycerophospholipid of *Mycoplasma fementans* labeled with a label substance, or a secondary antibody obtained by labeling an antibody against immunoglobulin of an immunized animal with a label substance, the antibody against the immunoglobulin of the immunized animal being prepared by using an animal other than the immunized animal used to prepare the anti-glycoglycerophospholipid antibody.

In still another aspect, the present invention provides a method for detecting a disease selected from AIDS, nephritis, and HTLV-I associated myelopathy, comprising the step of detecting the glycoglycerophospholipid having the foregoing properties (A) to (D), a substance having antigenicity similar to that of the glycoglycerophospholipid, or an antibody having reaction specificity to the glycoglycerophospholipid contained in blood.

In this specification, the glycoglycerophospholipid specifically existing in *Mycoplasma fementans* is simply referred to as "glycoglycerophospholipid", if necessary.

The present invention will be explained in detail below.

<1> Glycoglycerophospholipid of the present invention

The antibody of the present invention has reaction specificity to a glycoglycerophospholipid of *Mycoplasma fermentans*, which is prepared by using the glycoglycerophospholipid as an antigen. At first, the glycoglycerophospholipid of *Mycoplasma fementans* will be explained.

Existence of lipids inherent in cells infected with a retrovirus has been hitherto known. Five species of glycoglycerophospholipids (GGPLs: GGPL-I, GGPL-II, GGPL-III, GGPL-IV, GGPL-V) have been found in human helper T cells infected with HTLV-I. Among them, the structure of GGPL-I has been determined by the present inventors (Nishida et al., Nippon Nogeikagaku Kaishi, Vol. 68, No. 3 (1994), "Proceedings of 1994th Annual Meeting", p. 39). As for GGPLs other than GGPL-I, only their existence is acknowledged, and neither their physical properties nor their structures have been known.

The present inventors prepared lipid fractions from HTLV-I-infected human helper T cells (MT-4 (GGPL+)) in which GGPLs were found, and from cells of MT-4 (GGPL−) obtained by treating the cells of MT-4 (GGPL+) with an anti-mycoplasmal agent (MC201, produced by Dainippon Pharmaceutical). The prepared lipid fractions were separated by HPTLC (high-performance thin layer chromatography). Glycolipid was stained with the orcinol reagent, and phospholipid was stained with Dittmer reagent. As a result, two bands were detected (FIG. 4), which were found in MT-4 (GGPL+), and were not found in MT-4 (GGPL−). The two bands were also detected from MT-4 (GGPL−) cells obtained by cultivation with addition of a culture supernatant of MT-4 (GGPL+) cells previously passed through a filter having a pore size of 0.22 μm. As explained in Examples described later on, it was found that one of the two bands was GGPL-I, and the other was GGPL-III.

It has not been reported that any microorganism belonging to the genus Mycoplasma has, as a constitutional component, a glyceroglycophospholipid containing phosphocholine. It has been considered that GGPLs originate from human cells. However, it has been clarified from the result described above that GGPLs originate from *Mycoplasma fementans*. Therefore, it is assumed that *Mycoplasma fementans* can be detected if an antibody having reaction specificity to the glyceroglycophospholipid described above is obtained.

The glycoglycerophospholipid of *Mycoplasma fermentans* can be prepared from a culture of *Mycoplasma fermentans*. *Mycoplasma fementans* can be obtained, for example, as follows. A culture supernatant of cultured cells in which existence of GGPLs is confirmed ("GGPL -positive"), for example, a culture supernatant of MT-4 cells (human helper T cells infected with HTLV-I (human T lymphotropic retrovirus Type I)) is filtrated with a filter having a pore size of 0.22 μm. Thus *Mycoplasma fermentans* is obtained in a filtrate. Alternatively, it is also allowable to use a type strain such as *Mycoplasma fementans* PG18 strain.

Obtained *Mycoplasma fementans* is cultivated with, for example, an agar medium of PPLO broth (produced by Difco Laboratories) to isolate a colony which is then cultivated in a liquid medium such as PPLO broth (produced by Difco Laboratories) containing 10% (v/v) fetal bovine serum (FBS), 5% (w/v) yeast extract (produced by Flow Laboratories), 1,000 units/ml penicillin, 1% (w/v) dextrose, and 0.002% (w/v) phenol red. Thus cultivated microbial cells of *Mycoplasma fermentans* are obtained. Next, methanol is added to the microbial cells,of *Mycoplasma fementans*, followed by being left to stand for several hours.

The thus-obtained microbial cells are then subjected to ultrasonic treatment after chloroform is added thereto. The ultrasonic treated microbial cells is allowed to stand for several hours—therefor. Subsequently, the microbial cells are homogenized by using, for example, a Potter type TEFLON homogenizer to recover a supernatant. A lipid extract is obtained by evaporating the supernatant. The lipid extract thus obtained contains the glycoglycerophospholipid.

As described in Examples, the lipid fraction was applied to an HPTLC (high-performance thin layer chromatography) plate, which was developed with a mixed solvent of chloroform: methanol: 0.2% (w/v) calcium chloride aqueous solution=50:45:10 (v/v/v) to analyze phospholipid. As a result, six bands (Lipid i, Lipid ii, Lipid iii, Lipid iv, Lipid v, and Lipid vi) were detected (FIG. 3). According to the behavior on TLC, it was revealed that Lipid v and Lipid vi of them corresponded to GGPL-I and GGPL-III respectively. According to a result of FAB mass spectrometry, it was confirmed that GGPL-I was identical with Lipid v, and GGPL-III was identical with Lipid vi.

The glycoglycerophospholipid of *Mycoplasma fermentans* can be also obtained from MT-4 cells infected with *Mycoplasma fementans*. For example, MT-4 cells are cultured in RPMI-1640 medium added with 10% (v/v) FCS (fetal calf serum), and obtained cells are washed with PBS (phosphate buffered saline), from which lipids are extracted by using 400 ml of a mixed solution of chloroform: methanol (=2:1, 1:1, or 1:2).

The lipid extract of *Mycoplasma fementans* or MT-4 cells obtained as described above is divided into a non-adsorptive fraction (neutral fraction) and an adsorptive fraction (acid fraction) by using an anion exchange resin having diethylaminoethyl (DEAE) group such as DEAE-Sephadex A25 (produced by Pharmacia), and thus the non-adsorptive fraction is obtained. The non-adsorptive fraction is applied to a silica bead column, and fractionated with a concentration gradient based on chloroform/methanol/water (83:16:0.5 to 20:80:8 (v/v)). Thus GGPL-III can be separated from other phospholipids. Further, GGPL-I is isolated by performing elution with a concentration gradient based on 1-propanol/ aqueous ammonia/water (80:5:15 to 75:5:20).

Both of GGPL-I and GGPL-III are positive to the orcinol reagent, Dittmer reagent, and Dragendorff reagent (which stains choline), and they are degraded by a treatment with mild alkali. GGPL-I is negative to the ninhydrin reaction (which stains amino group), however, GGPL-III is positive to this reaction.

Results of physicochemical analysis performed by using purified GGPL-III are shown below.

(1) Infrared Absorption Spectrum

Absorption bands corresponding to —$CH_2$ and —$CH_3$ groups, hydroxyl group, estercarbonyl group, phosphate group, choline group, and primary amine group were detected respectively.

(2) Liquid Secondary Ionization Mass Spectrometry (LSIMS)

It was suggested that at least three species of fatty acids were present in the molecule. It was concluded that GGPL-III existed as at least four species of molecules, a major component of which had a molecular weight of 1048. Further, it was demonstrated that species of GGPL-III having molecular weights of 1020, 1076, and 1104 were also present.

(3) Tandem Mass Spectrometry (MS/MS)

It was suggested that phosphocholine was present in the molecule. It was concluded that the major component of GGPL-III had a molecular weight of 1048.

(4) Unidimensional $^1$H NMR Spectrum

Signals of glycerol, choline, and glucose were detected. Further, it was postulated that aminopropanediol was present. Accordingly, the spectrum of GGPL-III was compared with unidimensional $^1$H NMR spectrums obtained by using standard samples of 3-aminopropane-1,2-diol (1-aminopropane-2,3-diol) and 2-aminopropane-1,3-diol. As a result, it was suggested that GGPL-III possibly contained 2-aminopropane-1,3-diol as a constitutional component.

(5) Two-dimensional $^1$H NMR Spectrum (PH-DQF-COSY method)

A signal of proton originating from diacylglycerol was observed. A signal of proton of choline was also observed.

(6) Two-dimensional $^1$H- $^{31}$P NMR Spectrum

It was demonstrated that one molecule of GGPL-III contained two phosphorus atoms (P). It was postulated that a compound containing phosphorus bound to 1- or 6-position of a glucose residue. This position was highly possibly 6-position.

A structure of phosphocholine was suggested, in which a phosphate group bound to choline. A structure was postulated, in which a phosphate ester of aminopropanediol firstly bound to the 6-position of the glucose residue, and phosphocholine bound to the phosphoric ester of aminopropanediol.

According to the results described above, it has been revealed that GGPL-III is a novel glycoglycerophospholipid having the following properties:

(A) the glycoglycerophospholipid is reactive with orcinol reagent, Dittmer reagent, Dragendorff reagent, and ninhydrin reagent;

(B) the glycoglycerophospholipid is degradable with alkali;

(C) the glycoglycerophospholipid is obtained as a non-adsorptive fraction upon fractionation with an anion exchanger having DEAE group; and (D) the glycoglycerophospholipid has a molecular weight of 1048+28n measured by using a mass spectrometer, wherein n is −1, 0, 1, or 2.

According to the results described above, it was demonstrated that GGPL-III contained constitutional components of α-glucopyranosyl-(1'-3)-1,2-diacyl-sn -glycerol, phosphocholine, and phosphate ester of aminopropanediol. The phosphate ester of aminopropanediol was a phosphate ester of 2-aminopropane-1,3-diol. It was postulated that its binding site was 6'-position of the glucose reside of α-glucopyranosyl-(1'-3)-1,2-diacyl-sn-glycerol. It was further suggested that phosphocholine bound to the phosphate ester of 2-aminopropane-1,3-diol. The major component of GGPL-III had two palmitoyl groups as acyl groups, having its deduced structure as represented by the following formula (I). It was postulated that the major component of GGPL-III had the structure in which the phosphoric ester of 2-aminopropane-1,3-diol was inserted between phosphocholine and the glucose residue of GGPL-I (6'-O-phosphocholine-α-glucopyranosyl-(1'-3) -1,2-dipalmitoyl-sn-glycerol).

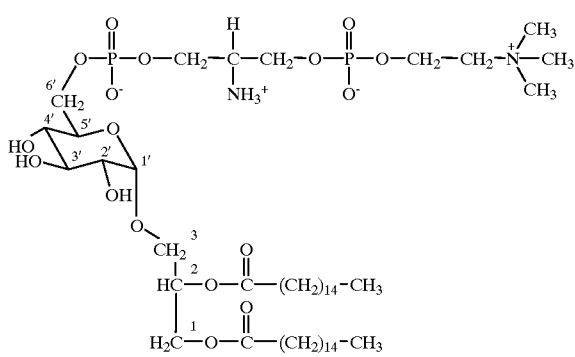

(I)

On the other hand, the other GGPL-III molecules having different molecular weights involve different types of acyl groups in α-glucopyranosyl-(1'-3)-1,2-diacyl-sn-glycerol. It is postulated that the molecule having a molecular weight of 1020 has a myristoyl group and a palmitoyl group, the molecule having a molecular weight of 1076 has a palmitoyl group and a stearoyl group, and the molecule having a molecular weight of 1104 has two stearoyl groups or a palmitoyl group and an eicosanoyl group. However, details are not clarified.

<2> Preparation of Antibody of the Present Invention

The antibody of the present invention is obtained by immunizing an animal with an antigen of the glycoglycerophospholipid originating from *Mycoplasma fermentans*, and separating serum from the animal. Alternatively, the antibody of the present invention is obtained by collecting antibody-producing cells of the animal, rendering the antibody-producing cells permanently culturable, and recovering the antibody from a culture thereof. The method for preparing the antibody of the present invention will be exemplarily described below. However, there is no limitation thereto. The antibody of the present invention may be prepared in accordance with other methods provided that the glycoglycerophospholipid of *Mycoplasma fermentans* is used as an antigen.

(1) Preparation of Polyclonal Antibody

Monophosphate lipid, Freund's complete adjuvant, and mineral oil are added to and mixed with the lipid extract of *Mycoplasma fementans* obtained as described above. PBS (phosphate buffered saline) containing 0.1% (v/v) Tween 80 is added thereto and emulsified.

Next, an obtained emulsion is subcutaneously or intraperitoneally administered to an animal such as mouse, rat, rabbit, guinea pig, or sheep. After priming immunization, boosting immunization is performed two or three weeks later in accordance with an ordinary method. Thus an antiserum having a high titer is obtained. Blood is collected one week after the final immunization, and serum is separated. The serum is heat-treated to inactivate complement. After that, an immunoglobulin fraction is obtained in accordance with a method similar to those used to purify an ordinary antibody, such as salting out with ammonium sulfate and ion exchange chromatography. Desirably, the increase in antibody titer in blood is confirmed in accordance-with, for example, enzyme immunoassay after the final immunization.

The antibody obtained as described above has reaction specificity to the glycoglycerophospholipid of *Mycoplasma fementans*, and it does not react with glycoglycerophospholipids of other mycoplasmas such as *Mycoplasma arthritidis* and *Mycoplasma hominis*.

A polyclonal antibody having reaction specificity to GGPL-III can be obtained by using purified GGPL-III instead of the lipid extract of *Mycoplasma fementans*.

(2) Preparation of Monoclonal Antibody

A monoclonal antibody is obtained in accordance with a method of Kohler and Milstein (*Nature*, pp. 495–492, 1975). Namely, antibody-producing cells of a mammalian, which produce an antibody against the glycoglycerophospholipid, is fused with myeloma cells to produce hybridomas. A hybridoma, which produces an objective antibody, is cloned, and the hybridoma is cultured. Thus the monoclonal antibody is obtained in a culture liquid. This process will be explained below while dividing the process into respective steps.

(i) Immunization of Animal and Preparation of Antibody-Producing Cells

Cells, which produce the antibody against the glycoglycerophospholipid, are obtained by immunizing an animal such as mouse, rat, rabbit, guinea pig, or sheep with the glycoglycerophospholipid, and preparing, for example, spleen cells, lymph node cells, or peripheral blood from the animal. The animal may be immunized with the glycoglycerophospholipid in the same manner as described in the item (1).

The monoclonal antibody having reaction specificity to GGPL-III may be obtained by immunizing an animal with purified GGPL-III. Alternatively, the monoclonal antibody may be obtained by preparing hybridomas by using antibody-producing cells of an animal immunized with a glycoglycerophospholipid mixture, and selecting a strain from the obtained hybridomas, the strain producing a monoclonal antibody having reaction specificity to GGPL-III. According to the latter method, it is unnecessary to obtain GGPL-III in an amount required to immunize the animal. It is sufficient to prepare GGPL-III in a minute amount of a degree capable of performing detection by the aid of enzyme immunoassay.

(ii) Preparation of Hybridoma

Antibody-producing cells are collected from the animal immunized with the glycoglycerophospholipid to perform cell fusion with myeloma cells. Various mammalian cell strains can be utilized as the myeloma cells to be used for cell fusion. However, it is preferred to use a cell strain which is the same species as the animal used to prepare the antibody-producing cells. In order to distinguish fused cells from non-fused cells after cell fusion, it is preferred to use a myeloma cell strain which has a marker so that non-fused myeloma cells may not survive, and only hybridoma cells may proliferate. For example, 8-azaguanine-resistant strain is deficient in hypoxanthine guanine phosphoribosyltransferase (HGPRT), and its nucleic acid synthesis depends on a de novo synthesis pathway. A fused cell (hybridoma) of such a myeloma cell and a normal antibody-producing cell is proliferative in a medium (HAT medium) containing hypoxanthine, aminopterin, and thymidine because the fused cell can synthesize nucleic acid by using a salvage circuit originating from lymphocyte owing to the presence of thymidine and hypoxanthine even when the de novo synthesis pathway is inhibited by aminopterin. On the contrary, the myeloma cells resistant to 8-azaguanine cannot synthesize nucleic acid, and the cells die because the de novo synthesis pathway is inhibited by aminopterin. Further, the antibody-producing cells as the normal cells cannot be cultured for a long period of time. Therefore, only the hybridoma cells produced by fusion of the antibody-producing cells and the myeloma cells can proliferate in the HAT medium. Accordingly, fused cells can be selected from non-fused cells (*Science*, Vol. 145, p. 709, 1964). A strain which secretes no inherent immunoglobulin is preferably used as the myeloma cell, in view of the fact that it is easy to obtain an objective antibody from a culture supernatant of an obtained hybridoma.

Cell fusion to obtain the hybridoma is performed, for example, as follows. A spleen is excised from the immunized animal, and it is suspended in RPMI 1640 medium to prepare a cell-floating suspension. The spleen cells are mixed with mouse myeloma cells such as SP2/0 cells (azaguanine-resistant, IgG-non-secretable: ATCC CRL-1581) at the logarithmic growth phase so that the ratio of spleen cells to the myeloma cells is about 10:1 to 1:1. After centrifugation, polyethylene glycol having an average molecular weight of 1,000 to 6,000 is added to a precipitate to give a final concentration of 30 to 50%. Thus the spleen cells and the myeloma cells are fused. Fusion may be performed by applying electric pulse to the cell mixture instead of the addition of polyethylene glycol.

The cells having been subjected to the fusion treatment are cultured with, for example, RPMI 1640 medium containing 10% (v/v) fetal calf serum (FCS), and then the cells are floated in a selective medium such as HAT medium. The cells are dispensed and poured into, for example, wells of a 96-well microtiter plate. Thus the cells are cultured so that only hybridomas are allowed to grow.

(iii) Screening for Hybridoma which Produces Antibody Having Reaction Specificity to Glycoglycerophospholipid The hybridomas obtained as described above are provided as a mixture of hybridomas which produce monoclonal antibodies against a plurality of antigens or epitopes respectively. Accordingly, it is significant to select, from the hybridomas, a strain which produces a monoclonal antibody having reaction specificity to the glycoglycerophospholipid, especially a monoclonal antibody having reaction specificity to GGPL-III. It is preferred to select a strain which produces a monoclonal antibody against an epitope having strong antigenicity, from monoclonal antibodies which bind to GGPL-III.

A strain, which produces a monoclonal antibody against the glycoglycerophospholipid, can be selected in accordance with an enzyme immunoassay by using the glycoglycerophospholipid as an antigen. Such a method includes an ELISA method comprising the following steps. Namely, the antigen is immobilized on a solid phase such as a microtiter plate, to which a culture liquid of a hybridoma is added, followed by addition of a secondary antibody labeled with, for example, an enzyme, a fluorescent substance, or a luminescent substance to perform incubation. Thus the antibody is detected by the aid of the bound label substance. In this method, an antibody may be immobilized on a solid phase, to which the antigen and a labeled secondary antibody may be successively added, followed by incubation. The ELISA method will be described in detail later on.

When no purified GGPL-III is obtained, the lipid fraction of *Mycoplasma fementans* is separated by using a high-performance thin layer chromatography (HPTLC) plate. A culture liquid of a hybridoma and a labeled secondary antibody are successively added to the plate, followed by incubation so that a position at which the label substance makes binding is detected. If the position is identical with a position of GGPL-III developed by HPTLC, the hybridoma is regarded to produce a monoclonal antibody against GGPL-III. Once the monoclonal antibody against GGPL-III is obtained, GGPL-III can be also purified from the lipid fraction in accordance with affinity chromatography or the like based on the use of the monoclonal antibody.

When it is confirmed that a well contains a hybridoma which produces an objective monoclonal antibody, cloning is performed from cells in the well containing the hybridoma in accordance with limiting dilution analysis or the like.

As demonstrated in Examples described later on, the hybridoma strain thus obtained, which produces the monoclonal antibody having reaction specificity to GGPL-III, has been deposited on May 24, 1994 in National Institute of Bioscience and Human Technology of Agency of Industrial Science and Technology of Ministry of International Trade and Industry under a deposition number of FERM P-14324, transferred to international deposition based on the Budapest Treaty on May 26, 1995, and awarded a deposition number of FERM BP-5115.

(iv) Preparation of Monoclonal Antibody

The monoclonal antibody of the present Invention is obtained in a culture supernatant by culturing the hybridoma obtained as described above in an appropriate medium. The monoclonal antibody can be purified in accordance with an ordinary method including, for example, salting out with ammonium sulfate, ion exchange chromatography, affinity chromatography based on the use of protein A or protein G, and immunoadsorption chromatography based on the use of an immobilized antigen.

The monoclonal antibody thus obtained makes no cross reaction with sialic acid-containing glycolipid (ganglioside) existing in serum of a healthy person not infected with *Mycoplasma fementans*, platelet activating factor (1-alkyl-2-acetylglycero-3-phosphocholine) or a partially deacylated product thereof, phosphatidylcholine or a partially deacylated product thereof, glycolipid, and phospholipid such as sphingomyelin.

The monoclonal antibody of the present invention can be used as it is. However, those obtained by fragmentation can be also used. Upon fragmentation of the antibody, it is indispensable for binding between the antigen and the antibody that the antigen-binding site (Fab) of the antibody is conserved. Therefore, it is possible to use a fragment containing the antigen-binding site (Fab), obtained by treating the antibody with a protease (for example, plasmin, pepsin, and papain) which does not degrade the antigen-binding site.

If a nucleotide sequence of a gene coding for the monoclonal antibody of the present invention or an amino acid sequence of the antibody is determined, it is possible to produce a fragment containing the antigen-binding site (Fab) in accordance with a technique of genetic engineering.

<3> Utilization of Glcoglycerphospholipid and Antibody thereagainst of the Present Invention The antibody of the present invention has reaction specificity to the glycoglycerophospholipid inherent in *Mycoplasma fementans*. Accordingly, the glycoglycerophospholipid in a specimen can be immunologically measured by using the antibody of the present invention. In this procedure, GGPL-I and GGPL-III can be measured by using the antibody which has reaction specificity to both of GGPL-I and GGPL-III. GGPL-III can be selectively measured by using the antibody which has reaction specificity to GGPL-III. When GGPL-III is measured, GGPL-III obtained as described above can be used as a standard substance. The glycoglycerophospholipid in a specimen includes a lipid fraction extracted from the specimen originating from a living body.

Those applicable to the immunological measurement include ordinary immunological methods based on the use of the antibody, such as ELISA methods and immunostaining methods. For example, the glycoglycerophospholipid in a specimen can be measured by allowing a specimen solution to contact with a solid phase including the anti-glycoglycerophospholipid antibody bound thereto so that the glycoglycerophospholipid contained in the specimen solution is bound to the antibody, separating and removing non-adsorptive components from the solid phase, subsequently allowing a glycoglycerophospholipid originating from *Mycoplasma fementans* labeled with a label substance to contact with the solid phase, making a competitive reaction between the glycoglycerophospholipid contained in the specimen solution and the labeled glycoglycerophospholipid, and detecting any one of the label substance bound to the solid phase and the label substance not bound to the solid phase.

Alternatively, the glycoglycerophospholipid in a specimen can be measured by allowing a specimen solution and a glycoglycerophospholipid labeled with a standard substance to contact with a solid phase including the anti-glycoglycerophospholipid antibody bound thereto, allowing the glycoglycerophospholipid contained in the specimen solution and the labeled glycoglycerophospholipid to make a competitive reaction with the antibody, and detecting any one of the label substance bound to the solid phase and the label substance not bound to the solid phase. In this procedure, a non-labeled standard glycoglycerophospholipid may be used in place of the labeled glycoglycerophospholipid to perform a competitive reaction between the glycoglycerophospholipid in the specimen and the standard glycoglycerophospholipid, followed by allowing the anti-glycoglycerophospholipid antibody labeled with a label substance to contact with the solid phase so that any one of the label substance bound to the solid phase and the label substance not bound to the solid phase is detected. A labeled secondary antibody may be also used in this procedure.

Further, it is allowable that the glycoglycerophospholipid in a specimen solution is bound to a solid phase, with which a labeled anti-glycoglycerophospholipid antibody is allowed to contact so that any one of the label substance bound to the solid phase and the label substance not bound to the solid phase is detected.

It is also allowable that a standard glycoglycerophospholipid is bound to a solid phase, with which a specimen solution and a labeled anti-glycoglycerophospholipid antibody are allowed to contact so that any one of the label substance bound to the solid phase and the label substance not bound to the solid phase is detected. A labeled secondary antibody may be also used in this procedure. GGPL-III in a specimen can be measured by using purified GGPL-III as the standard glycoglycerophospholipid.

Further, the anti-glycoglycerophospholipid antibody in a specimen can be measured by allowing a specimen solution to contact with a solid phase including the anti-glycoglycerophospholipid bound thereto so that the anti-glycoglycerophospholipid antibody contained in the specimen solution is bound to the antibody, separating and removing non-adsorptive components from the solid phase, subsequently making a reaction with a secondary antibody obtained by labeling an anti-human immunoglobulin antibody with a label substance, and detecting the label substance. The glycoglycerophospholipid of the present invention is inherent in *Mycoplasma fementans*. Accordingly, it is possible to know the presence or absence of infection with *Mycoplasma fementans* by inspecting the presence or absence of the anti-glycoglycerophospholipid antibody in a specimen.

Besides the foregoing, various variations are known as methods for the immunological measurement. Any of the methods can be applied to the present invention.

Other than the method based on the use of the solid phase as described above, those adoptable in the present invention include methods to be used for immunologically measuring haptens and antibodies, such as a liquid phase method comprising the steps of allowing a glycoglycerophospholipid in a specimen and a labeled glycoglycerophospholipid to make a competitive reaction with the antibody described above, separating the antigen bound to the antibody from the free antigen by using, for example, polyethylene glycol, dextran, or a secondary antibody, and detecting a label substance of the free labeled antigen.

Those usable as the solid phase include ordinary materials such as agarose beads, latex particles, and wells of microtiter plates composed of, for example, polystyrene or nylon, regardless of their forms (for example, particles, fine particles, test tubes, microtiter plates, and strips). It is preferred to perform blocking by using, for example, BSA (bovine serum albumin) or gelatin after the antibody or the glycoglycerophospholipid is bound to the solid phase. Those usable as the label substance include, for example, enzymes capable of color development of a dye based on an enzyme reaction, such as peroxidase and alkaline phosphatase; radioisotopes; and fluorescent dyes such as fluorescein isothiocyanate.

As for the dye, for example, 4-chloro-1-naphthol, O-phenylenediamine (OPD), or 3,3'-diaminobenzidine is used for peroxidase, and p-nitrophenylphosphate is used for alkaline phosphatase.

*Mycoplasma fementans* has the glycoglycerophospholipid according to the present invention. Therefore, *Mycoplasma fementans* can be detected by using the anti-glycoglycerophospholipid antibody of the present invention. For example, *Mycoplasma fementans* in a specimen can be detected by extracting a lipid fraction from the specimen, allowing the extracted lipid fraction to contact with a solid phase so that the lipid is adsorbed to the solid phase, reacting the solid phase including the lipid adsorbed thereto with the antibody of the present invention, simultaneously or subsequently making a reaction with an anti-immunoglobulin antibody labeled with a label substance and reactive with the antibody, and detecting the label substance.

Further, the glycoglycerophospholipid concerning the present invention is inherent in *Mycoplasma fermentans*. Therefore, *Mycoplasma fementans* can be also detected by measuring a glycoglycerophospholipid contained in a specimen in accordance with the method as described above, and relating the presence or absence of the glycoglycerophospholipid or an existing amount thereof to the presence or absence of *Mycoplasma fermentans* or an existing amount thereof in the specimen.

Those usable as the specimen in the method for detecting the glycoglycerophospholipid or the method for detecting *Myconlasma fermentans* described above include, for example, blood, serum, plasma, cerebro-spinal fluid, urine, synovial fluid, and cultured cell solution (supernatant).

Besides the foregoing methods, *Mycoplasma fermentans* can be also detected by reacting the anti-glycoglycerophospholipid antibody labeled with a label substance, with a tissue or cells of a living organism exactly or after applying a treatment for immobilizing a glycoglycerophospholipid, binding the labeled antibody to the tissue or cells of the living organism infected with *Mycoplasma fementans*, and detecting the label substance. Those usable as a method for the immobilizing treatment include, for example, methods based on the use of formalin, glutaraldehyde, and paraformaldehyde. Alternatively, *Mycoplasma fementans* may be also detected by reacting a non-labeled anti-glycoglycerophospholipid antibody instead of the anti-glycoglycerophospholipid antibody labeled with the label substance with a tissue or cells of a living organism subjected to an immobilizing treatment, simultaneously or subsequently making a reaction with a secondary antibody obtained by labeling an antibody against immunoglobulin of an immunized animal with a label substance, the antibody against the immunoglobulin of the immunized animal having been prepared by using an animal other than the immunized animal used to prepare the antibody, binding the labeled secondary antibody to the tissue or cells of the living organism infected with Mycoplasma fementans, and detecting the label substance.

Upon detection of the glycoglycerophospholipid or Mycoplasma fementans contained in a specimen by immunological methods, the detection can be conveniently performed by previously preparing a reagent kit comprising the antibody having reaction specificity to the glycoglycerophospholipid of Mycoplasma fementans, and a secondary antibody obtained by labeling an antibody against immunoglobulin of an immunized animal with a label substance, the antibody against the immunoglobulin of the immunized animal being prepared by using an animal other than the immunized animal used to prepare the antibody having reaction specificity to the glycoglycerophospholipid of Mycoplasma fementans.

The kit is specifically exemplified by a kit comprising, for example, a microtiter plate, a blocking reagent such as BSA (bovine serum albumin), the glycoglycerophospholipid of Mycoplasma fementans (standard substance), the antibody of the present invention, a peroxidase-labeled anti-mouse IgG antibody, an aqueous solution of hydrogen peroxide, OPD, and a washing buffer. It is preferred that the antibodies, the glycoglycerophospholipid of Mycoplasma fementans, and other pertinent components of the kit are provided as lyophilized preparations or dissolved solutions in a solvent capable of stably storing them.

The detection of Mycoplasma fementans can be utilized for the following diagnosis methods.

(1) Prediction of Crisis of Retrovirus Infectious Disease

It is reported that Myconlasma fermentans is an exacerbation factor of AIDS (acquired immunodeficiency syndrome) (Lo, S. -C. et al., 1993, Res. Microbiol., 144, 489–493). Crisis of AIDS does not necessarily occur even when a patient is infected with HIV (human immunodeficiency virus). Usually, AIDS has a long latent period, and complex infection of Mycoplasma fermentans participates in crisis of AIDS. It is conceived that Mycoplasma fementans also participates in crisis of infectious diseases caused by other retroviruses.

Lipids extracted from various species of mycoplasmas were added to a culture liquid of cells latently infected with HIV, at certain lipid concentrations (final concentrations) as shown in Table 1, and the cells were cultured. A number of destroyed cells was inspected by using an optical microscope, which was used as an index of frequency of induction of expression of HIV. Results are shown in Table 1.

TABLE 1

| Species of Mycoplasma | Lipid concentration (μg/ml) | Inducing activity |
| --- | --- | --- |
| M. fermentans | 550 | +++ |
| M. hyorhinis | 310 | ± |
| M. orale | 1090 | − |

TABLE 1-continued

| Species of Mycoplasma | Lipid concentration (μg/ml) | Inducing activity |
| --- | --- | --- |
| M. salivarium | 1090 | − |
| M. hominis | 490 | + |
| M. arthritidis | 600 | − |

According to the results and the foregoing report, it is understood that Mycoplasma fementans has an activity to induce proliferation of the retrovirus. Therefore, it is possible to predict the crisis by inspecting the presence or absence of complex infection of Mycoplasma fementans with, for example, blood of a patient infected with the retrovirus. Thus it is possible to take an appropriate treatment.

(2) DiaQnosis of Rheumatism

It is reported that Mycoplasma fementans is a cause of rheumatism (Williams, M. H. et al., Lancet ii: 277–280 (1970)). Therefore, it is expected that morbidity of rheumatism can be diagnosed by detecting Mycoplasma fementans by using the antibody of the present invention.

(3) Application to Targeting Therapy

It is expected to apply and utilize the antibody of the present invention for preventing crisis of retrovirus diseases and curing rheumatism such that an anti-HIV agent such as azidothymidine or dideoxyinosine and/or an anti-mycoplasmal agent is bound to the antibody of the present invention to be administered to a patient infected with the retrovirus or a patient of rheumatism.

(4) Utilization an Neutralizing Antibody for Treatment

The antibody of the present invention is expected to present an activity as a neutralizing antibody which binds to Mycoplasma fementans to avoid infection caused by Mycoplasma fementans. Administration of the antibody to a living body makes it possible to use the antibody for curing or preventing infectious diseases caused by viruses having high possibility of complex infection of Mycoplasma fementans.

(5) Diagnosis of Nephritis

As demonstrated in Examples described later on, a lipid, to which the anti-glycoglycerophospholipid antibody of the present invention binds, is highly frequently found in blood of patients of nephritis. It has been suggested that nephritis can be diagnosed by detecting the lipid. The lipid is distinguished from GGPL-III judging from the position on HPTLC. However, the lipid is considered to be a lipid having antigenicity similar to that of GGPL-III because the monoclonal antibody which recognizes GGPL-III binds to the lipid. The substance having antigenicity similar to that of GGPL-III can be immunologically measured by using the anti-glycoglycerophospholipid antibody of the present invention.

BRIEF DESCRIPTION OF THE DRAWINGS

FIG. 1 shows a result of electrophoresis of amplified products obtained by first step PCR for spacer regions between 16S–23S ribosome RNA genes of various mycoplasmas, wherein:

1: Mycoplasma fementans GGPL strain separated from MT-4 cells;
2: Mycoplasma fementans PG18;
3: Myconlasma hyorhinis DBS1050;
4: Mycoplasma arginini G230;
5: Mycoplasma orale CH19299;
6: Mycoplasma salivarium PG20;

7: *Mycoplasma penetrans* GTU-54-6A1;

8: negative control.

Figure 2:
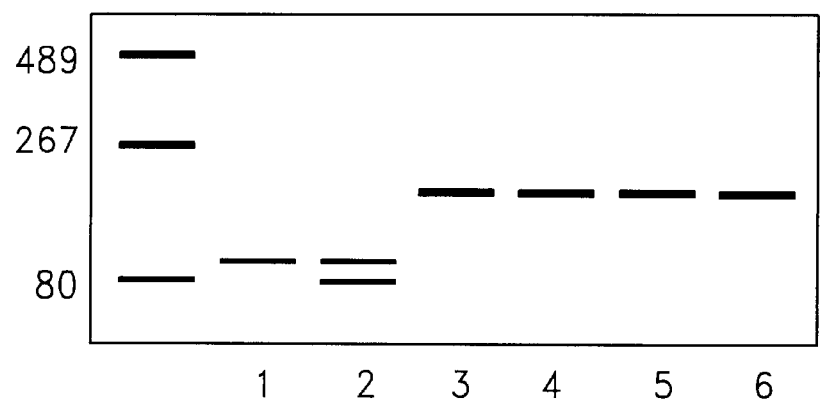

FIG. 2 shows a result of electrophoresis of fragments obtained by digesting, with various restriction enzymes, amplified products obtained by second step PCR for a spacer region between 16S–23S ribosome RNA genes of *Mycoplasma fementans*, wherein 1: VspI, 2: HindIII, 3: ClaI, 4: HincII, 5: HaeIII, 6: no treatment.

Figure 3:
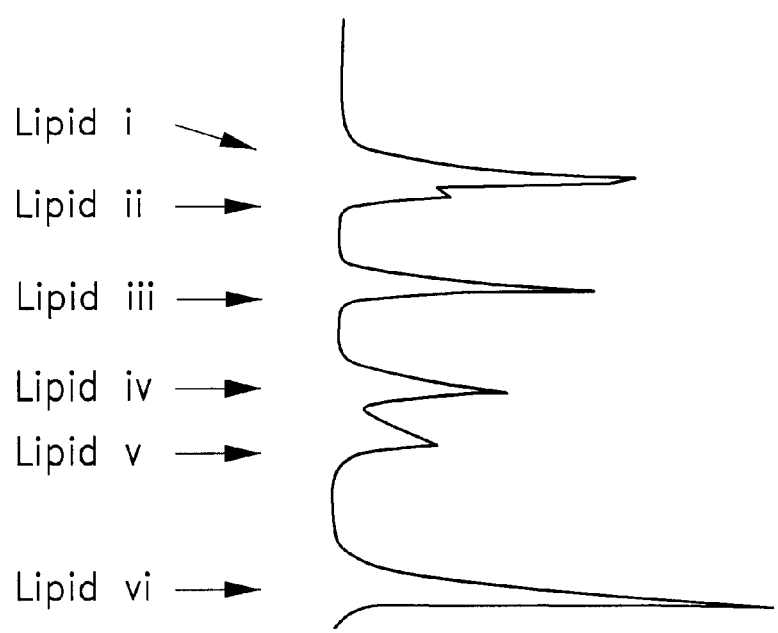

FIG. 3 shows a TLC pattern (densitometry) of phospholipids contained in a lipid fraction of *Mycoplasma fementans*.

Figure 4:
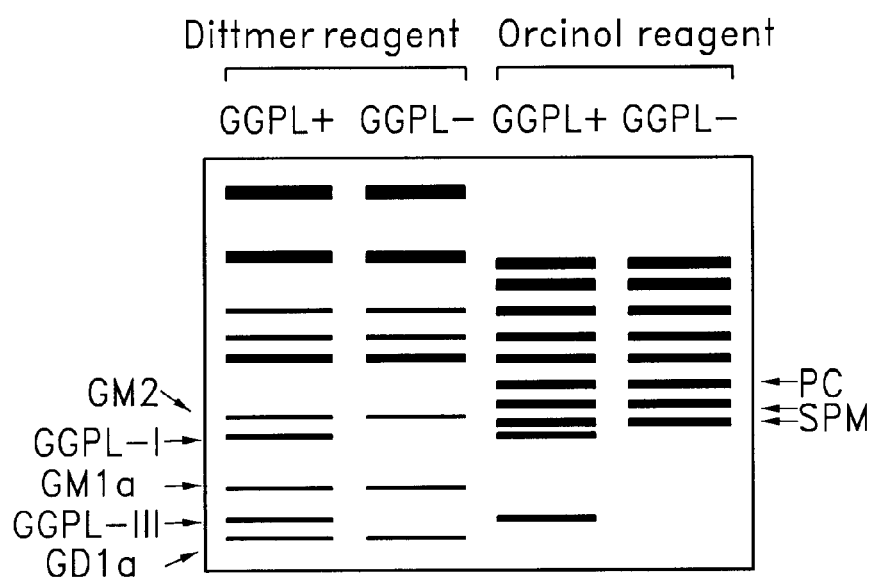

FIG. 4 shows a TLC pattern of phospholipids and glycolipids contained in lipid fractions of MT-4 cells infected or not infected with *Mycoplasma fementans*, wherein PC indicates phosphatidylcholine, and SPM indicates sphingomyelin.

Figure 5:
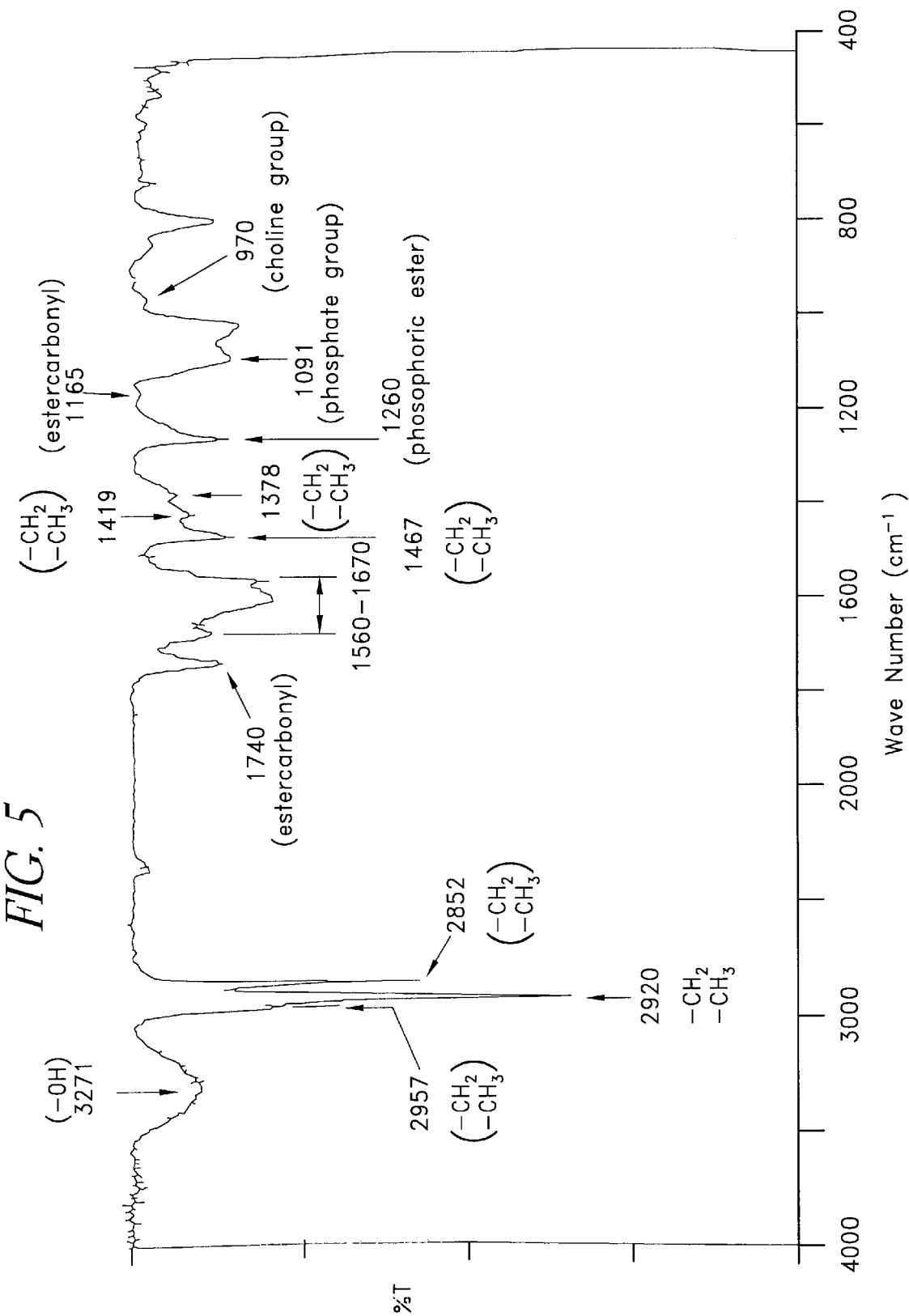

FIG. 5 shows an infrared absorption spectrum of GGPL-III.

Figure 6:
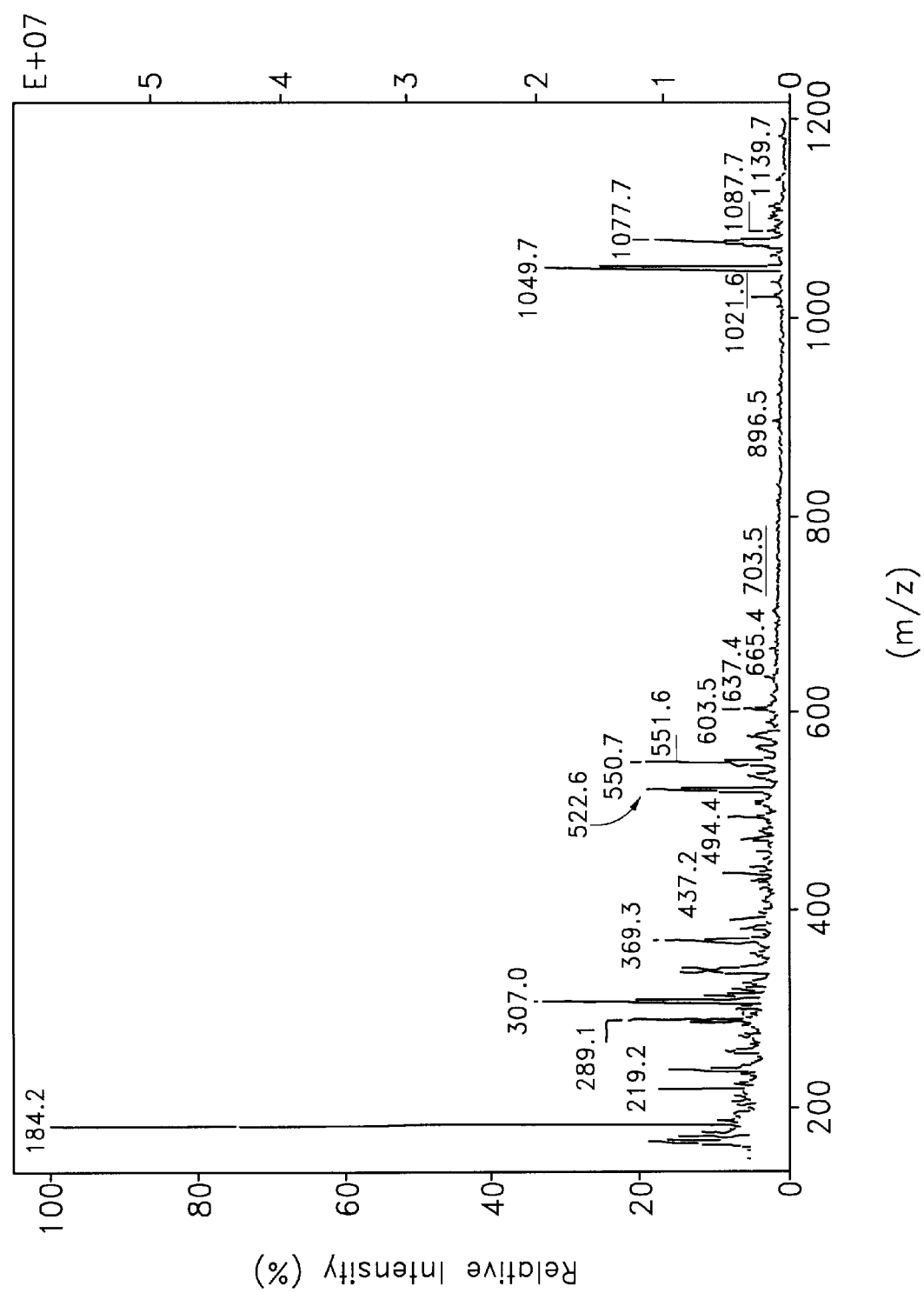

FIG. 6 shows a liquid secondary ion mass spectrum of GGPL-III obtained by the (+) method.

Figure 7:
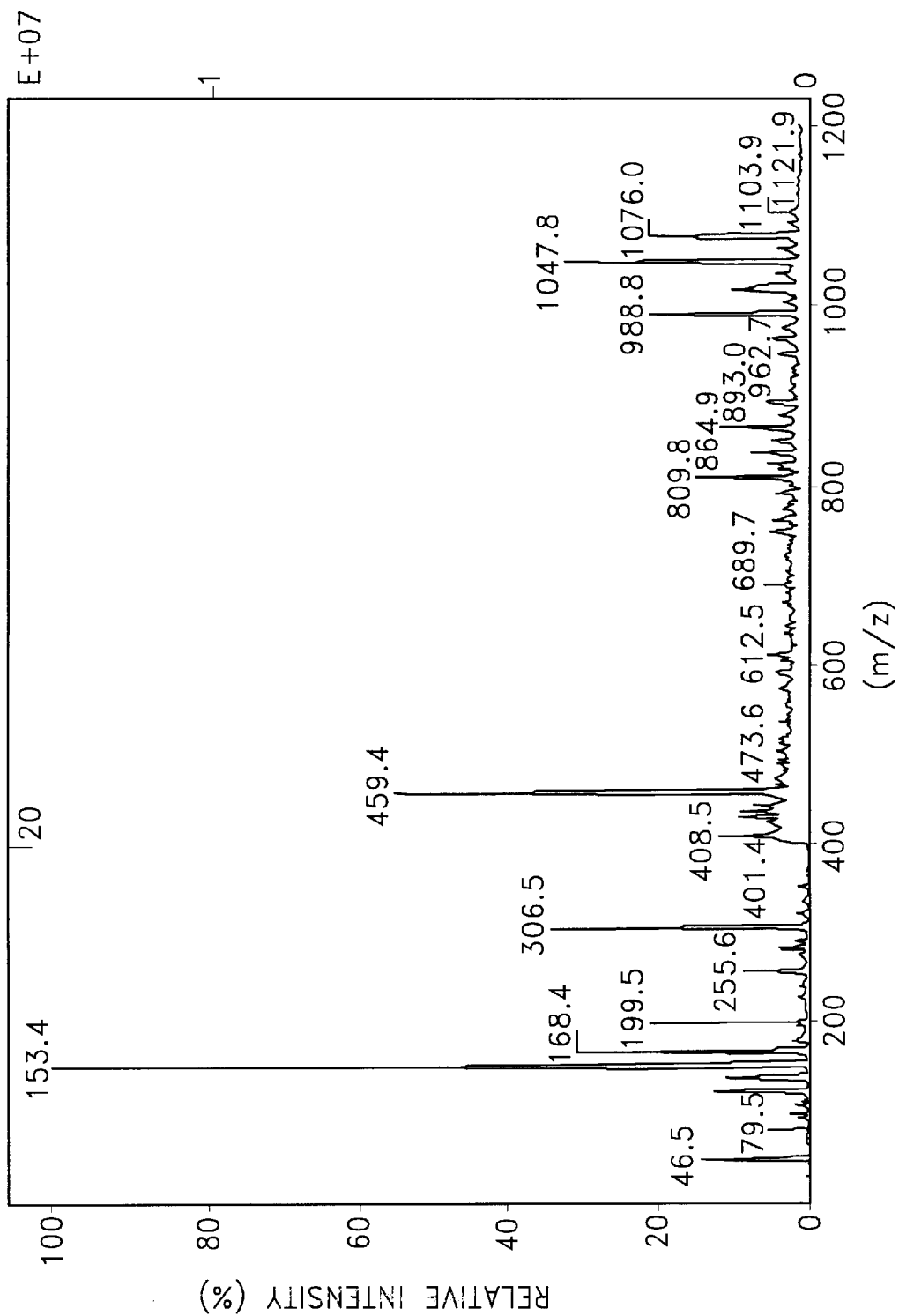

FIG. 7 shows a liquid secondary ion mass spectrum of GGPL-III obtained by the (−) method.

Figure 8:
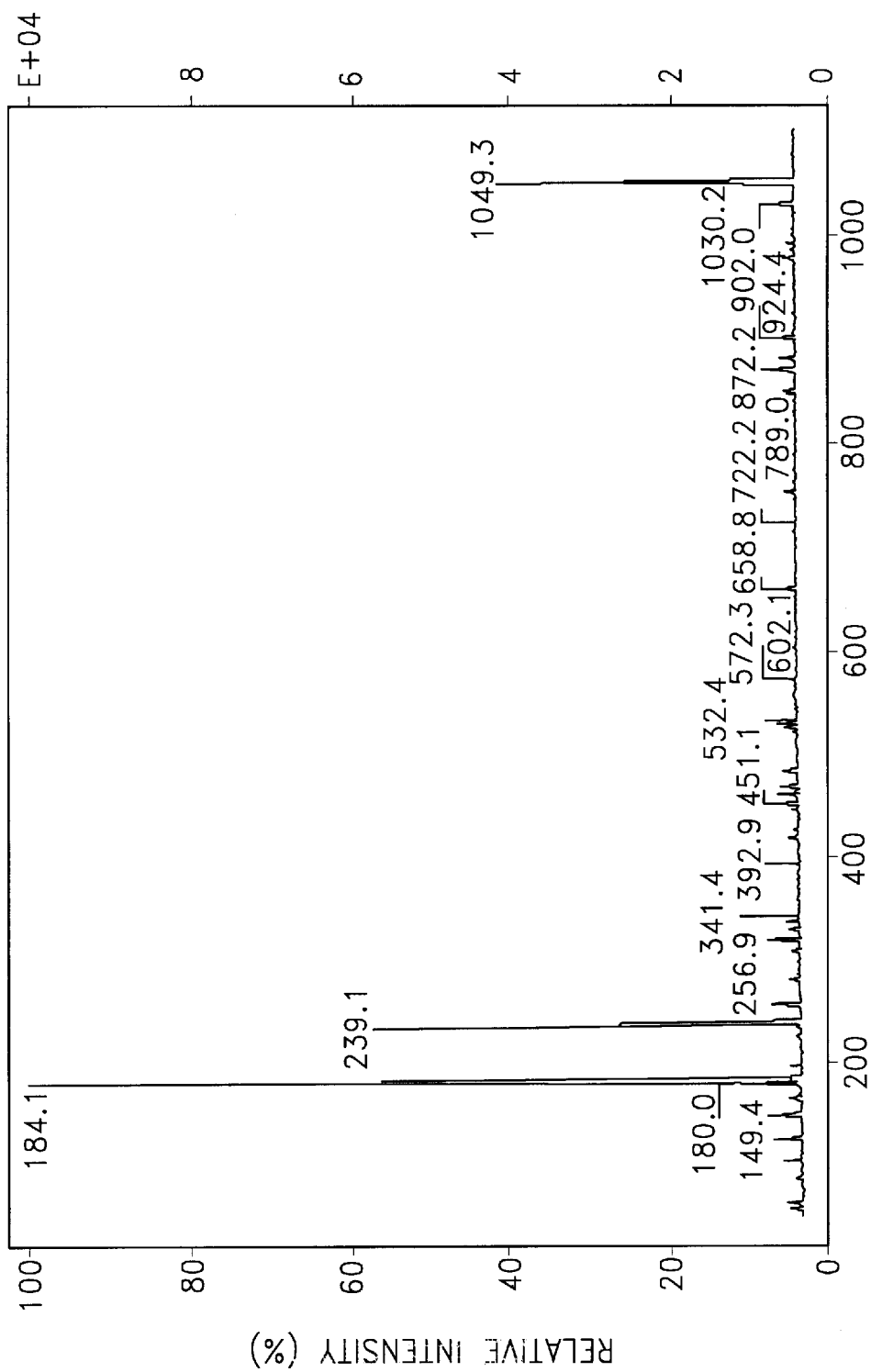

FIG. 8 shows a tandem mass spectrum of GGPL-III obtained by the (+) method.

Figure 9:
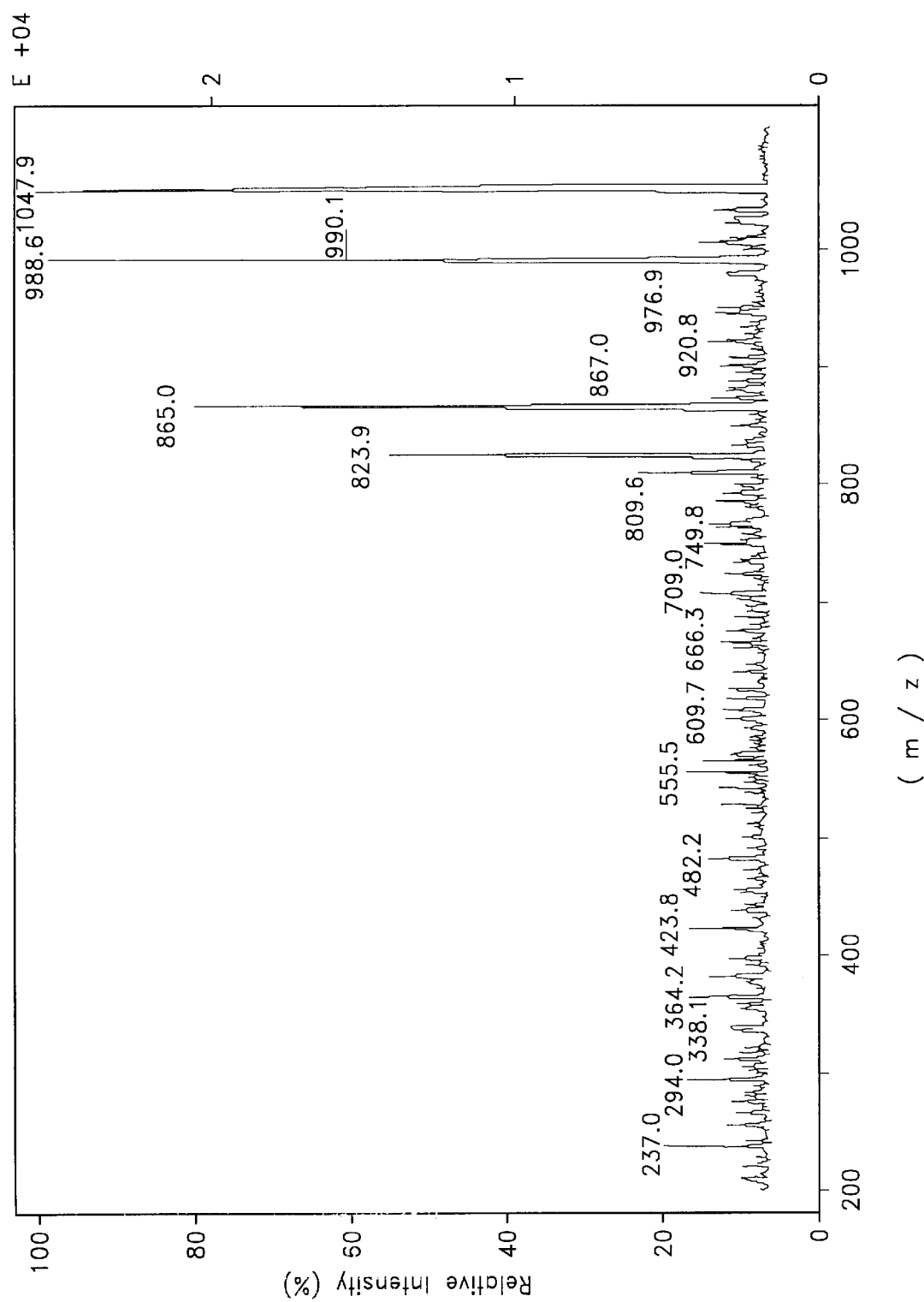

FIG. 9 shows a tandem mass spectrum of GGPL-III obtained by the (−) method.

Figure 10:
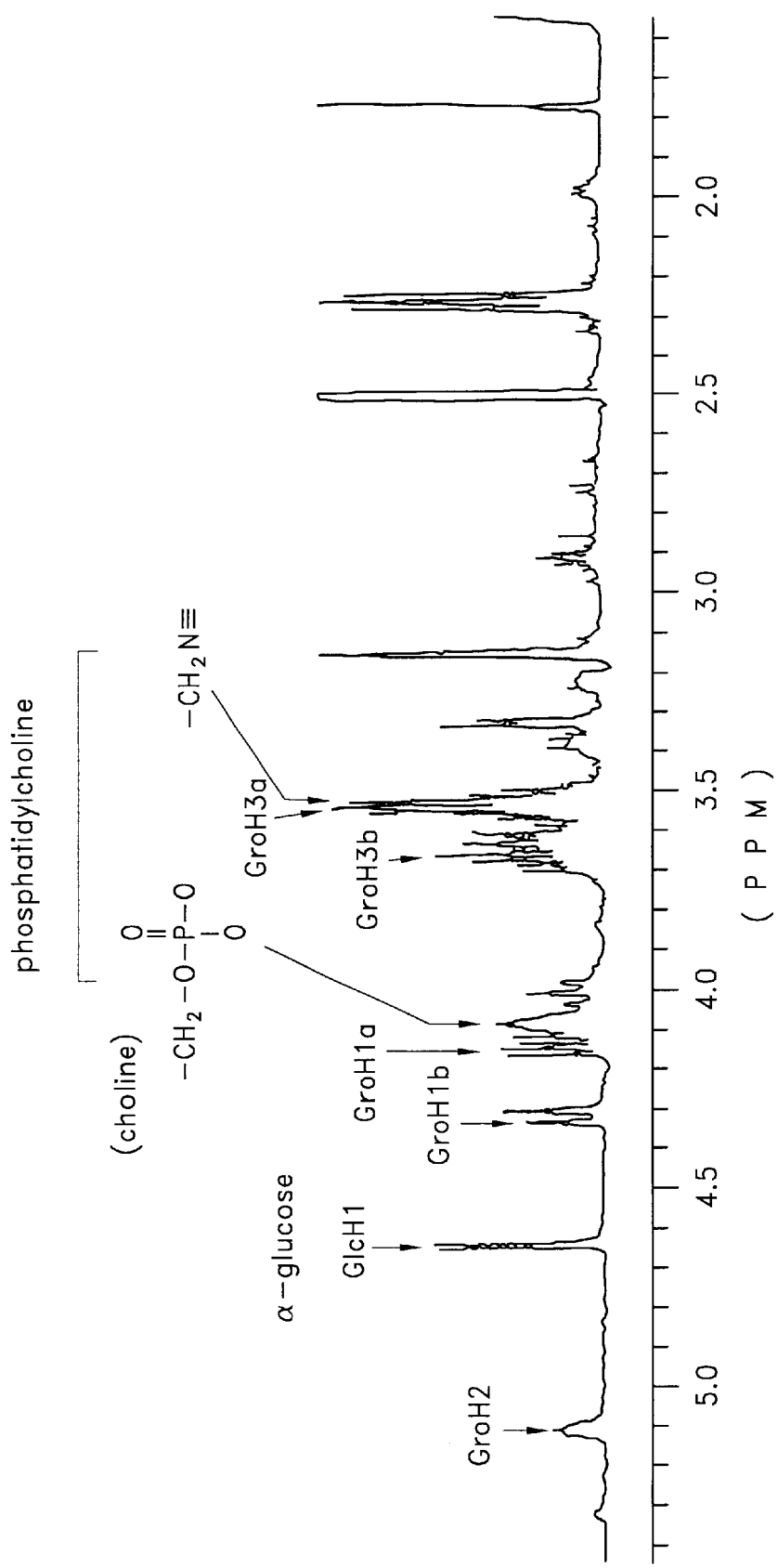

FIG. 10 shows a unidimensional $^1$H NMR spectrum.

Figures 11A, 11B:
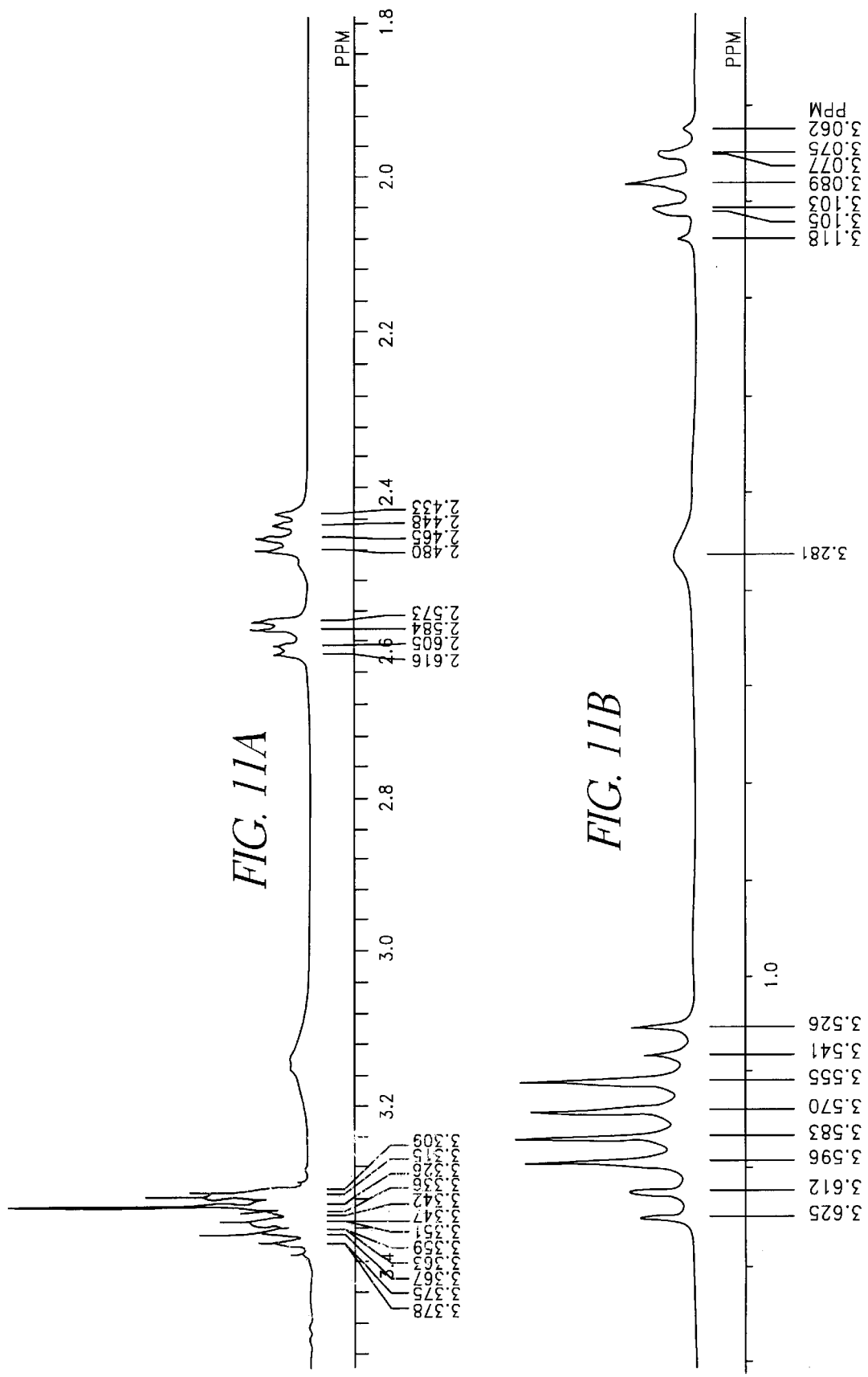

FIG. 11 shows unidimensional $^1$H NMR spectrums of 3-aminopropane-1,2-diol (1-aminopropane-2,3-diol) (A) and 2-aminopropane-1,3-diol (B).

Figure 12:
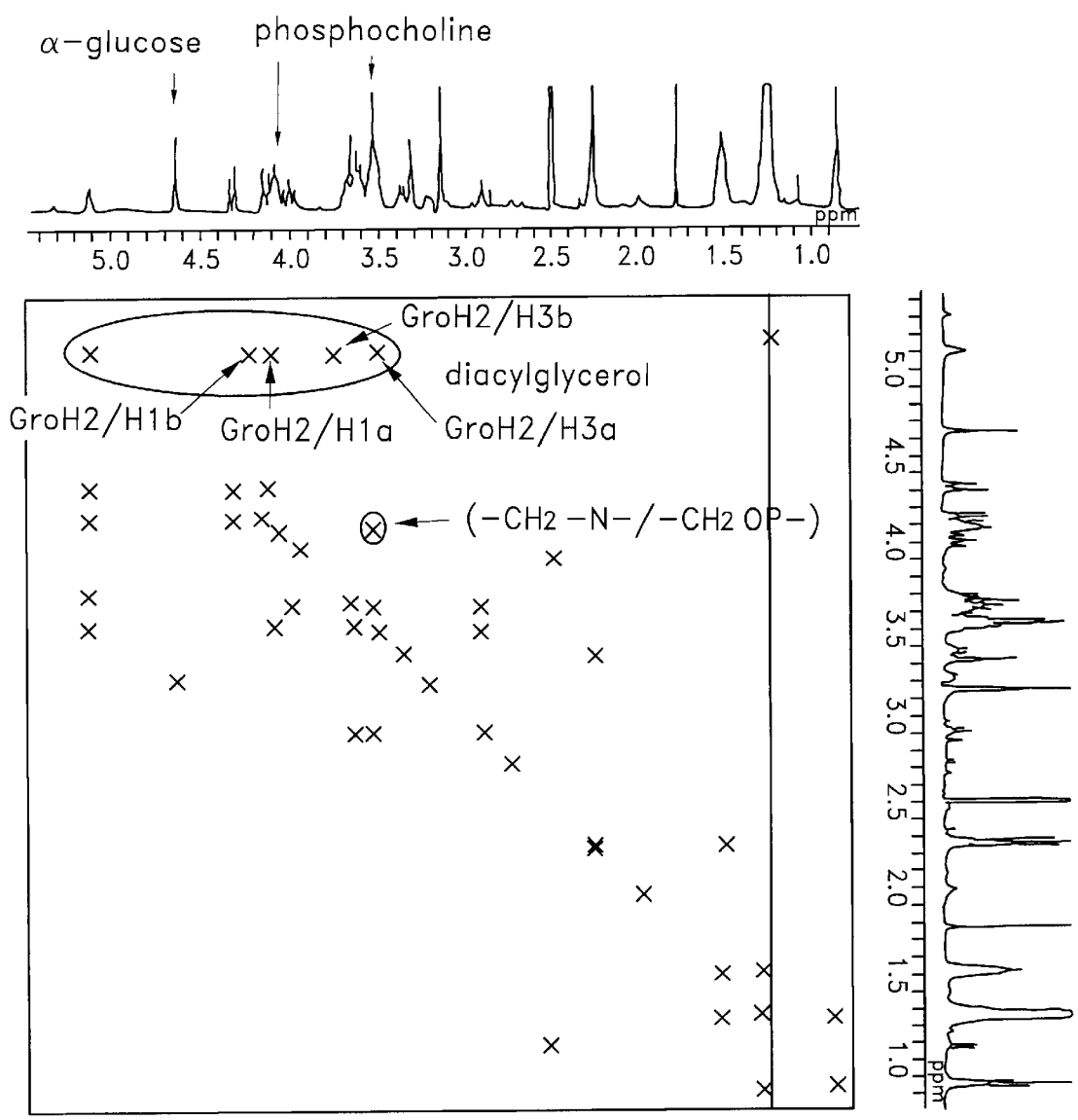

FIG. 12 shows a two-dimensional $^1$H NMR spectrum of GGPL-III obtained by the PH-DQF-COSY method.

Figure 13:
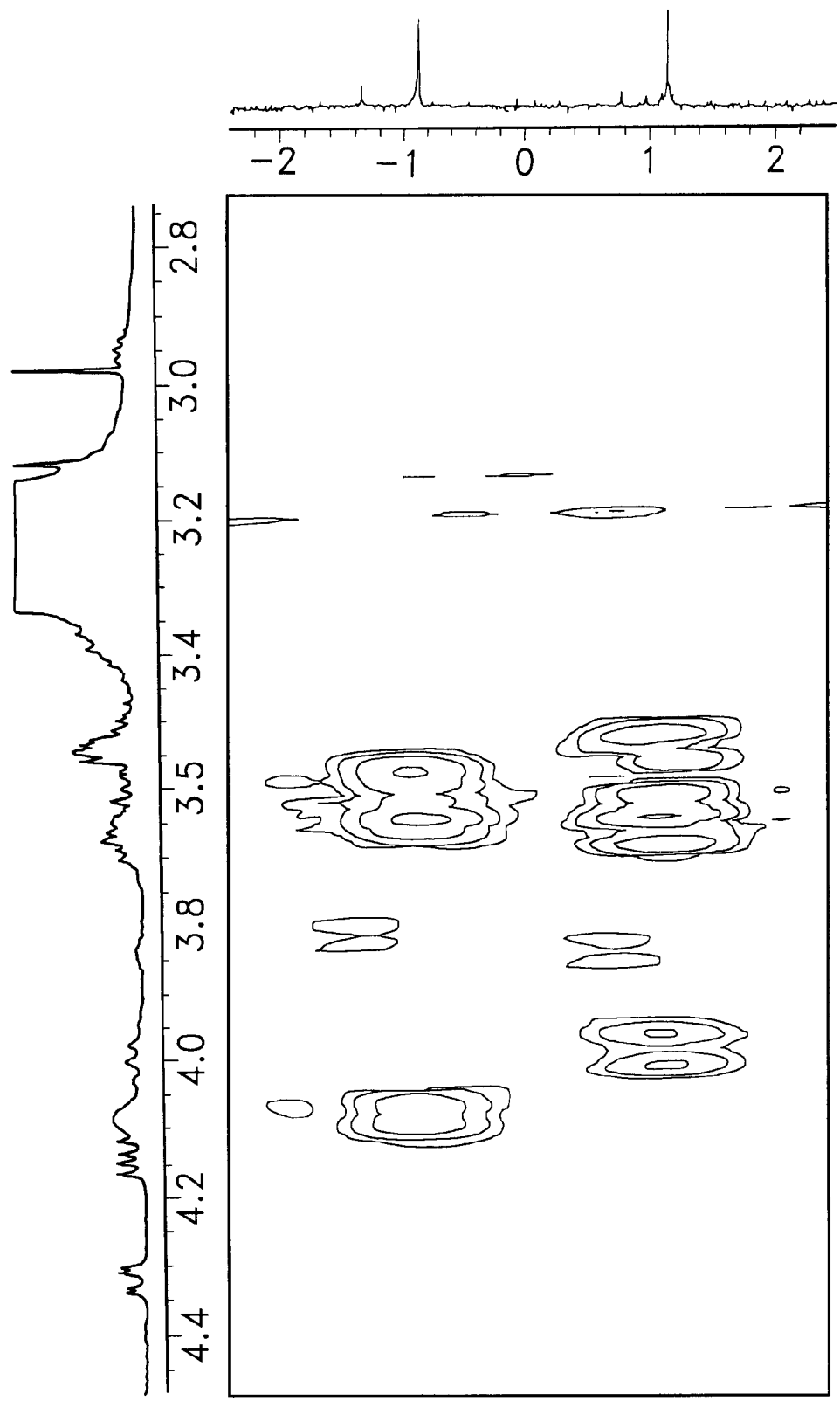

FIG. 13 shows a two-dimensional $^1$H-$^{31}$P NMR spectrum of GGPL-III.

Figure 14:
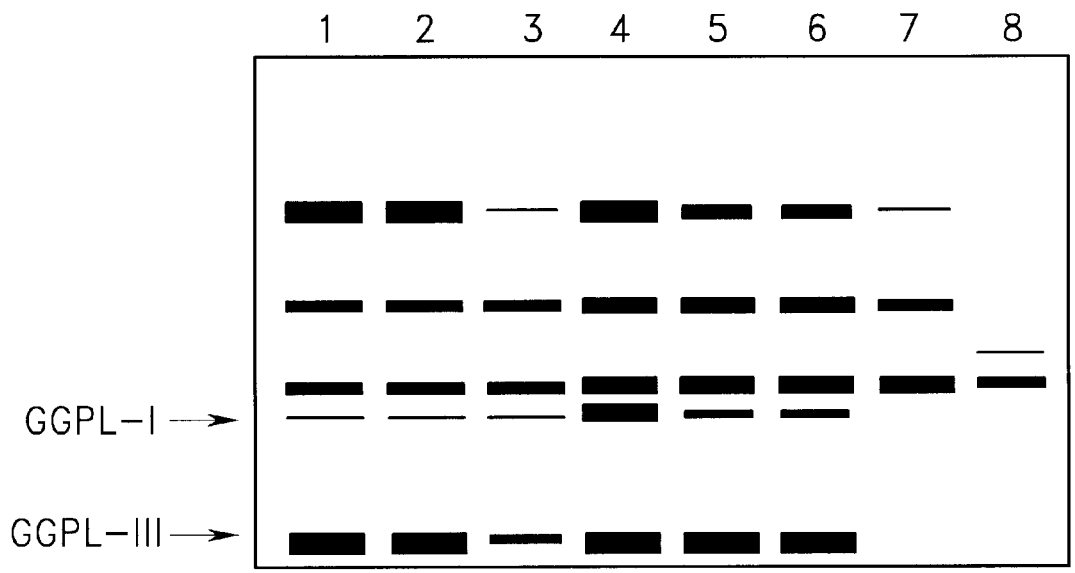

FIG. 14 shows a result of TLC of phospholipids contained in lipid fractions of various mycoplasmas (stained with Dittmer reagent), wherein:

1: *Mycoplasma fementans* GGPL strain;

2: *Mycoplasma fementans* incognitus;

3: *Mycoplasma fementans* PG18 strain;

4: *Mycoplasma fementans* F17 strain;

5: *Mycoplasma fementans* F1 strain;

6: *Mycoplasma fementans* F7 strain;

7: MVcoplasma arthritidis;

8: *Mycoplasma hominis*.

Figure 15:
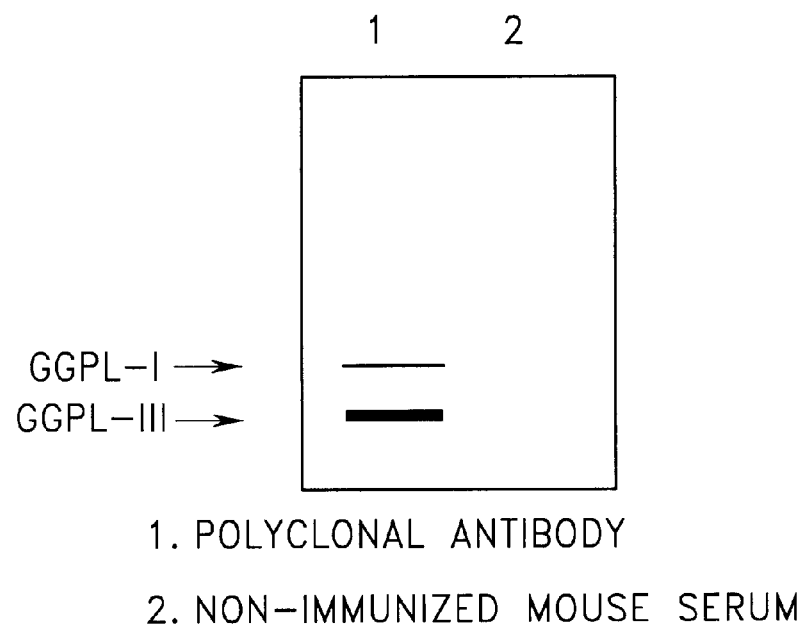

FIG. 15 shows a result obtained by immunostaining a lipid fraction of MT-4 cells separated by HPTLC, by using a polyclonal antibody described in Example 2.

Figure 16:
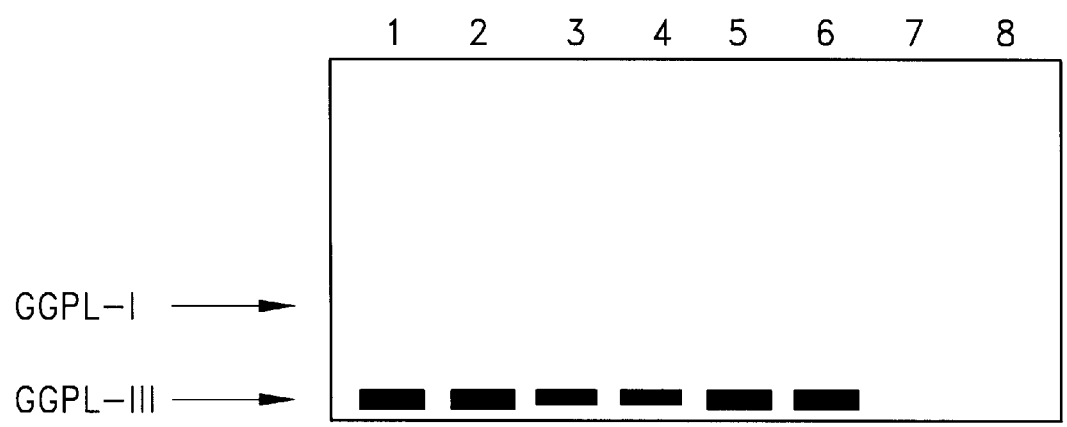

FIG. 16 shows a result obtained by immunostaining lipid fractions of various mycoplasmas separated by HPTLC, by using a monoclonal antibody described in Example 3 (reference numerals indicate the same contents as those depicted in FIG. 14).

Figure 17:

FIG. 17 shows a photograph illustrating a result obtained by immunostaining MT-4 cells infected with *Mycoplasma fementans*, by using the monoclonal antibody of the present invention.

Figure 18:
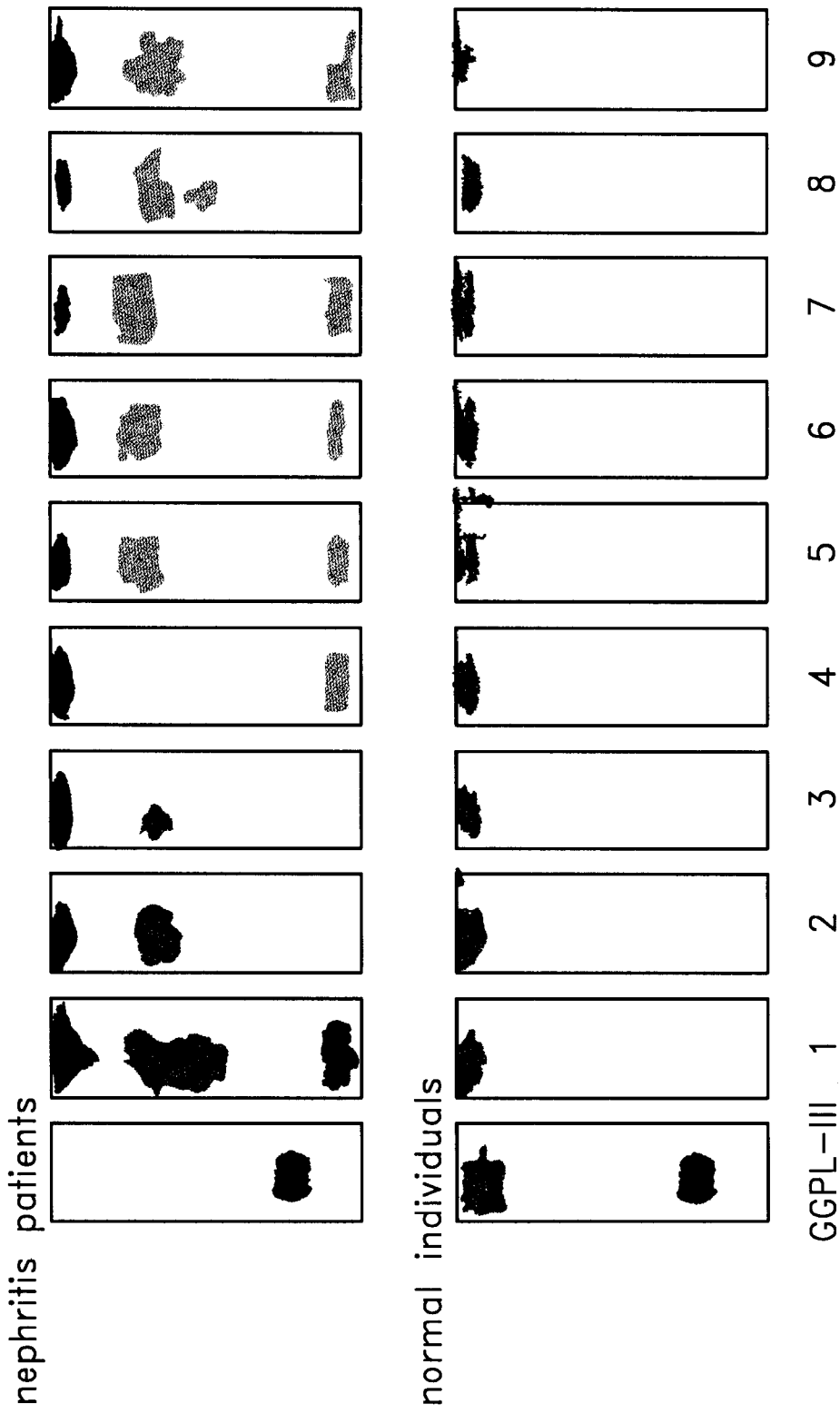

FIG. 18 shows results obtained by immunostaining lipids extracted from blood samples of patients of nephritis or normal individuals and separated by HPTLC, by using the monoclonal antibody described in Example 3, wherein "nephritis patients" indicates results for lipids extracted from blood samples of patients of nephritis, and "normal individuals" indicates results for lipids extracted from blood samples of normal individuals.

BEST MODE FOR CARRYING OUT THE INVENTION

The present invention will be explained more specifically below in accordance with Examples.

EXAMPLE 1

Isolation and Structural Analysis of Novel Glycoglycerophospholipid

<1> Cultivation of *Mycoplasma fementans* and Preparation of Lipids

A culture supernatant of MT-4 cells (human helper T cell strain infected with human T lymphotropic retrovirus Type I (HTLV-I)) containing GGPLs was filtrated with a filter having a pore size of 0.22 μm. An obtained filtrate was inoculated to an agar medium of PPLO broth (produced by Difco Laboratories) to perform cultivation. Colonies were isolated and then cultivated in a liquid medium of PPLO broth (produced by Difco Laboratories) containing 10% (v/v) fetal bovine serum (FBS), 5% (w/v) yeast extract (produced by Flow Laboratories), 1,000 units/ml penicillin, 1% (w/v) dextrose, and 0.002% (w/v) phenol red. Formed colonies were fried egg-shaped. Thus it was confirmed that the obtained microorganism was a mycoplasma.

Figure 1:
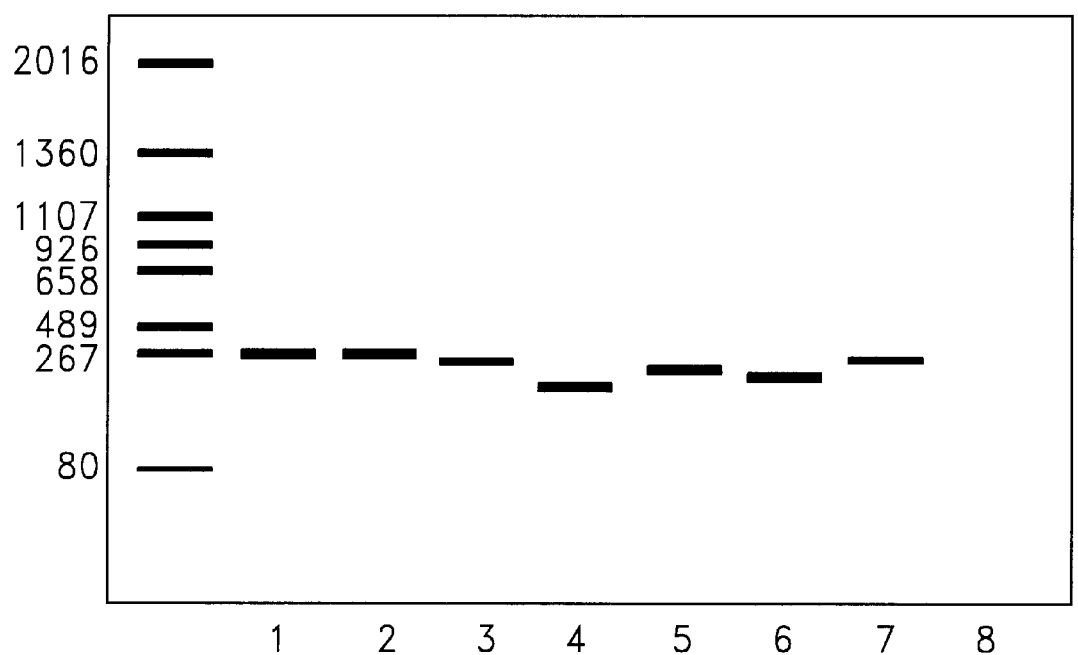

DNA was prepared from this microorganism. The spacer region between 16S–23S ribosome RNA genes, which might differ depending on the mycoplasmal species, was analyzed by means of two-step PCR (Harasawa, R. et al., 1993, *Res. Microbiol.*, 144: 489–493) for respective mycoplasmal species of *Mycoplasma fementans* isolated from MT-4 cells, *Mycoplasma fementans* type strain PG18, *Mycoplasma hyorhinis* DBS1050 (ATCC 17981), *Mycoplasma arginini* G230 (ATCC 23838), *Mycoplasma orale* CH19299, *Mycoplasma salivarium* PG20 (ATCC 23064), and *Mycoplasma penetrans* GTU-54–6A1. As a result, a product of first step PCR of this microorganism was coincident with that of PG18 strain as the type strain of *Mycoplasma fermentans* (FIG. 1). Further, an amplified product, which was obtained by second step PCR by using the PCR product, was digested with VspI and HindIII, and was not digested with ClaI, HincII, and HaeIII (FIG. 2). Thus this microorganism was identified to be *Mycoplasma fermentans*, which was designated as GGPL strain (*M. fermentans* GGPL strain).

Methanol (100 ml) was added to microbial cells (1 g) of *Mycoplasma fermentans* obtained by cultivation in accordance with the method described above, followed by being left to stand for several hours. Chloroform (200 ml) was added thereto, and the preparation was subjected to an ultrasonic treatment, followed by being left to stand for several hours. The preparation was homogenized with a Potter type Teflon homogenizer to obtain a homogenate which was centrifuged at 10,000 rpm to recover a supernatant thereof. The supernatant was evaporated, and thus a lipid extract (50 mg) was obtained.

<2> Analysis of Lipid Fraction of *Mycoplasma fementans*

The lipid fraction of *Mycoplasma fementans* obtained as described above was applied to an HPTLC (high-performance thin layer chromatography) plate (produced by Merck), and developed with a mixed solvent of chloroform: methanol: 0.2% (w/v) calcium chloride aqueous solution=50:45:10 (v/v/v). The phospholipid was stained with Dittmer reagent. A phospholipid pattern was measured on the basis of absorption at 580 nm by using a TLC densitometer (CS910, produced by Shimadzu). As a result, six bands (Lipid i, Lipid ii, Lipid iii, Lipid iv, Lipid v, and Lipid vi) were detected (FIG. 3).

Lipid fractions were extracted from MT-4 cells infected with *Mycoplasma fementans* and MT-4 cells obtained by treating the former cells with an anti-mycoplasmal agent (MC201, produced by Dainippon Pharmaceutical) in accordance with a known method (Bligh and Dyer, *Can. J. Biochem. Physiol.*, 37, 911–917 (1959)). Respective extracts of the lipid fractions were applied to an HPTLC (high-performance thin layer chromatography) plate (produced by Merck), and developed with a mixed solvent of chloroform: methanol: 0.2% (w/v) calcium chloride aqueous solution =50:45:10 (v/v/v). The glycolipid was stained with the orcinol reagent, and the phospholipid was stained with Dittmer reagent. As a result, two bands were detected, which were found in MT-4 (GGPL+), and were not found in MT-4 (GGPL−) (FIG. 4). One of the two bands was identified to be GGPL-I with its structure having been already known, and the other was identified to be GGPL-III. Other Dittmer reagent-positive bands were identified to be GM2, GM1a, and GD1a, and other orcinol reagent-positive bands were identified to be phosphatidylcholine and sphingomyelin (Matsuda, K. et al., *Biochem. Biophys. Acta,* 1168, 123–129 (1993)).

A lipid fraction was extracted from MT-4 cells (treated with the anti-mycoplasmal agent PC201) cultured with addition of a culture supernatant of MT-4 cells (infected with *Mycoplasma fementans* ) passed through a filter having a pore size of 0.22 μm. The extracted lipid fraction was analyzed by HPTLC in the same manner as described above. As a result, the two bands described above were detected. Therefore, it is clear that the two bands, i.e., GGPL-I and GGPL-III originate from *Mycoplasma fementans.*

According to the behavior on TLC, it was revealed that GGPL-I and GGPL-III corresponded to Lipid v and Lipid vi described above originating from *Mycoplasma fermentans* respectively. According to results of FAB mass spectrometry, it was confirmed that GGPL-I was identical with Lipid v, and GGPL-III was identical with Lipid vi.

Extraction was performed from MT-4 cells (60 ml, wet volume) infected with *Mycoplasma fementans* by using solvents of chloroform: methanol=2:1, 1:1, and 1:2 (400 ml) to obtain a total lipid of 993 mg. The total lipid was applied to a DEAE Sephadex A-25 column to separate it into a non-adsorptive fraction (neutral fraction) and an adsorptive fraction (acid fraction). Thus 775 mg of the non-adsorptive fraction was obtained. The non-adsorptive fraction was applied to an Iatrobeads column (produced by Iatron), and fractionated three times with a concentration gradient of chloroform/methanol/water (83:16:0.5 to 20:80:8, v/v/v). Finally, elution was performed with a concentration gradient of 1-propanol/aqueous ammonia/water (80:5:15 to 75:5:20, v/v/v) to isolate 3 mg of GGPL-III.

<3> Structural Analysis of GGPL-III

GGPL-III was positive to the orcinol reagent, Dittmer reagent, and Dragendorff reagent, and it was degraded by a treatment with mild alkali. GGPL-I was negative to the ninhydrin reaction, however, GGPL-III was positive to the ninhydrin reaction. According to these results, it was revealed that GGPL-III was a glycophospholipid containing choline.

Further, structural analysis of GGPL-III was performed as described below.

(1) Measurement of Infrared Absorption Spectrum

An infrared absorption spectrum of GGPL-III was measured by using an infrared spectrophotometer (FTIR -8100M, produced by Shimadzu) equipped with an infrared microscope (IMS-8000, produced by Shimadzu). A result is shown in FIG. 5.

As a result, absorption bands were detected, corresponding to $-CH_2$ group and $-CH_3$ group (2957, 2920, 2852, 1467, 1419, 1378 $cm^{-1}$), hydroxyl group (3271 $cm^{-1}$), estercarbonyl group (1740, 1165 $cm^{-1}$), phosphate group (1091 $cm^{-1}$), choline group (970 $cm^{-1}$), and primary amine group (1560 to 1670 $cm^{-1}$) respectively.

(2) Liquid secondary ion mass sPectrometry (LSIMS)

GGPL-III purified as described above (about 1 μg) was dissolved in a mixed solution (1 μL) of chloroform: methanol (1 volume: 1 volume). 3-Nitrobenzyl alcohol in the case of the (+) method or triethanolamine in the case of the (−) method was added and mixed to the solution, as a matrix in an amount of 0.5 mL. The obtained mixed solution was used as a sample to perform liquid secondary ion mass spectrometric analysis by using a TSQ 70 triple quadrupole type mass spectrometer (produced by Finnegan MAT). Cesium ion ($Cs^+$) accelerated to 20 keV was used as a primary ion flow. The spectrum was obtained at a velocity of 250 atomic mass unit (amu)/sec. A spectrum obtained by the (+) method is shown in FIG. 6, and a spectrum obtained by the (−) method is shown in FIG. 7.

As a result, ions were observed in the (+) method at m/z=1021, m/z=1049, and m/z=1077. According to this fact, it was suggested that at least three species of GGPL-III molecules having different fatty acid compositions existed. It was concluded that a major component of GGPL-III was represented by a peak of m/z=1049, having its molecular weight of 1048 obtained by subtracting a mass of proton of 1 from 1049. It was also concluded that the other components had molecular weights of 1020 and 1076.

In the (−) method, ions were observed at m/z=1047, m/z=1076, and m/z=1103. Judging from combination with the spectrum analysis based on the (+) method, it was suggested that at least four species of GGPL-III molecules having different fatty acid compositions existed. It was concluded that a major component of GGPL-III observed by the (−) method was represented by a peak of m/z=1047, having its molecular weight of 1048 obtained by adding a mass of proton of 1 to 1047. It was also concluded that another component had a molecular weight of 1104. A molecular weight deduced from the ion of m/z=1076 was 1077. However, a molecular weight of 1076 was deduced from the result of the (+) method. A difference between this molecular weight and the molecular weight of another component corresponded to an amount of two methylene groups. Accordingly, it was concluded that the molecular weight was 1076.

(3) Tandem Mass Spectrometry (MS/MS)

Samples, which were prepared in the same manner as the samples used for LSIMS (a sample for the (+) method and a sample for the (−) method), were used to measure tandem mass spectrums by using a TSQ 70 triple quadrupole type mass spectrometer (produced by Finnegan MAT). Cesium ion ($Cs^+$) accelerated to 20 keV was used as a primary ion flow. Algon, which was maintained at 0.26 pascal (2.0 mTorr), was used as a CAD (low energy collisionally activated dissociation) gas. The spectrum was obtained at a velocity of 250 atomic mass unit (amu)/sec. A spectrum obtained by the (+) method is shown in FIG. 8, and a spectrum obtained by the (−) method is shown in FIG. 9.

As a result, ions were observed at m/z=184 and m/z=1049 in the (+) method. According to the presence of the ion of m/z=184, it was suggested that phosphocholine was present in the molecule of GGPL-III. It was concluded that the molecular weight of GGPL-III was 1048 obtained by subtracting a mass of proton of 1 from 1049. In the (−) method, an ion of m/z=1047 was observed. According to this fact, it was concluded that the molecular weight of GGPL-III was 1048 obtained by adding a mass of proton of 1 to 1047. It was supported that among the plurality species of GGPL-IIIs suggested by LSIMS, the molecule having the molecular weight of 1048 was the major component.

(4) Unidimensional $^1H$ NMR Spectrum

GGPL-III (500 μg) substituted with deuterium ($^2H$), phosphatidylcholine (2 mg), and D-glucose 6-phosphate disodium salt (produced by Oriental Yeast) (about 200 μg) were dissolved in 0.5 mL of a solvent composed of [$^2$H] dimethyl sulfoxide (($C^2H_3)_2$SO): $^2H_2$O (98 volumes: 2 volumes) respectively to obtain $^1$H-NMR spectrums at 60° C. at 400 MHz by using a GX-400 spectrometer (produced by JEOL). Tetramethylsilane was used as a standard.

An integrated value of a signal of glucose (GlcH1) was regarded as 1.00 to standardize the spectrum, and intensities of the other signals are quantified. A result is shown in FIG. 10.

As a result, signals of glycerol (Gro) were detected at 4.319 ppm (GroH1b), 4.145 ppm (GroH1a), 5.118 ppm (GroH2), [3].677 ppm (GroH3b), and 3.562 ppm (GroH3a). Signals of choline were detected at 4.074 ppm (—POCH$_2$—), 3.529 ppm (—CH$_2$≡), and 3.139 ppm (—N (CH$_3$)$_3$). The spectrum of GGPL-III was compared with unidimensional $^1$H NMR spectrums obtained by the foregoing method by using standard samples of 3-aminopropane-1,2-diol (1-aminopropane-2,3-diol) and 2-aminopropane-1,3-diol respectively (see FIGS. 11A and 11B respectively). As a result, it was found that 2-aminopropane-1,3-diol was highly possibly contained in GGPL-III. Further, a signal at 4.647 ppm (GlcH1) was conspicuously detected as a signal of glucose (Glc).

(5) Two-dimensional $^1$H NMR Spectrum

Samples prepared in the same manner as those used for the unidimensional $^1$H NMR spectrum were used to perform two-dimensional $^1$H NMR analysis at 60 ° C. at 400 MHz in accordance with the PH-DQF-COSY method with a width of 2,000 Hz for each dimension by using an FX-400 spectrometer (produced by JEOL). A result is shown in FIG. 12.

As a result, signals of protons originating from diacylglycerol were observed (GroH2/H1b, GroH2/H1a, GroH2/H3b, GroH2/H3a in FIG. 12). Signals of protons of choline were observed (—CH$_2$—N—/—CH$_2$OP— in FIG. 12).

(6) Two-dimensional $^1$H-$^{31}$ P NMR Spectrum

Samples prepared in the same manner as those used for the unidimensional $^1$H NMR were used to obtain a two-dimensional $^1$H-$^{31}$ P HMQC spectrum at 60° C. at 400 MHz by using an FX-400 spectrometer (produced by JEOL). A result is shown in FIG. 13.

As a result, a spectrum equivalent to that obtained by $^1$H NMR described above was obtained for the first dimension ($^1$H NMR), and two signals were obtained from the second dimension ($^{31}$ p NMR). This fact suggests that two phosphorus atoms (P) are contained in one molecule of GGPL-III.

No crossing peak was detected between positions in the first dimension at which signals of 2-, 3-, 4-, and 5-protons of glucose residue appeared (in the vicinity of 2.9 to 3.0 ppm) and positions in the second dimension at which signals of phosphorus appeared (−0.9 ppm and 1.1 ppm). Accordingly, it was postulated that a compound containing phosphorus bound to 1-position or 6-position of glucose residue. Further, crossing peaks were detected between a signal of 6a-proton of glucose residue (in the vicinity of 4.0 ppm in the first dimension) and a signal of phosphorus in the second dimension (−0.9 ppm), and between a signal of 6b-proton of glucose residue (in the vicinity of 3.6 ppm in the first dimension) and signals of phosphorus in the second dimension (−0.9 ppm and 1.1 ppm) respectively.

Further, a crossing peak was detected between a signal of choline in the first dimension (about 4.05 to about 4.1 ppm) and a signal of phosphorus in the second dimension (−0.9 ppm). Accordingly, it was possible to assume a structure of phosphocholine in which phosphate group bound to choline. Further, the crossing peak of phosphocholine deviated from the signal of 6a-proton of glucose residue (in the vicinity of 4.0 ppm in the first dimension). Accordingly, a structure was postulated, in which phosphoric ester of aminopropanediol firstly bound to 6-position of glucose residue, and phosphocholine further bound to phosphoric ester of aminopropanediol.

Judging from summarization of the foregoing results, GGPL-III is a novel glycoglycerophospholipid having the following properties:

(A) the glycoglycerophospholipid is reactive with orcinol reagent, Dittmer reagent, Dragendorff reagent, and ninhydrin reagent;

(B) the glycoglycerophospholipid is degradable with alkali;

(C) the glycoglycerophospholipid is obtained as a non-adsorptive fraction upon fractionation with an anion exchanger having DEAE group; and (D) the glycoglycerophospholipid has a molecular weight of 1048+28n measured by using a mass spectrometer, wherein n is −1, 0, 1, or 2.

Further, it has been demonstrated from the foregoing results that GGPL-III comprises constitutional components of α-glucopyranosyl-(1'-3)-1,2-diacyl-sn -glycerol, phosphocholine, and phosphoric ester of aminopropanediol. The phosphoric ester of aminopropanediol is a phosphoric ester of 2-aminopropane-1,3-diol. It is postulated that its binding site is 6'-position of glucose residue of α-glucopyranosyl-(1'-3)-1,2-diacyl-sn-glycerol. Further, it is suggested that phosphocholine binds to the phosphoric ester of 2-aminopropane-1,3-diol.

The respective GGPL-III molecules having the different molecular weights have different types of acyl groups in α-glucopyranosyl-(1'-3)-1,2-diacyl-sn -glycerol. It is postulated that any acyl group in the major component (molecular weight 1048) is palmitoyl group. An entire deduced structure is one as represented by the foregoing formula (I). The GGPL-III molecules having other molecular weights are different in length of the acyl group. It is postulated that the molecule having the molecular weight of 1020 has a myristoyl group and a palmitoyl group, the molecule having the molecular weight of 1076 has a palmitoyl group and a stearoyl group, and the molecule having the molecular weight of 1104 has two stearoyl groups or a palmitoyl group and an eicosanoyl group. However, details are not clarified.

<4> Analysis of Lipid Components of Various Species of Mycoplasmas

Various species of mycoplasmas (Mycoplasma fermentans GGPL strain, Mycoplasma fementans incognitus (ATCC 53949), Mycoplasma fementans PG18 strain, Mycoplasma fementans F17 strain, Mycoplasma fementans F1 strain, Mycoplasma fementans F7 strain, Mycoplasma arthritidis, and Mycoplasma hominis (ATCC 15488)) were cultivated in a liquid medium of PPLO broth (produced by Difco Laboratories) containing 10% (v/v) FBS (fetal bovine serum), 5% (w/v) yeast extract (produced by Flow Laboratories), 1,000 units/ml penicillin, 1% (w/v) dextrose, and 0.002% (w/v) phenol red. Lipids were extracted from obtained culture liquids in accordance with a known method (Bligh and Dyer, Can. J. Biochem. Physiol., 37, 911–917 (1959)). The lipid extracts were applied to an HPTLC plate (produced by Merck), and developed with a mixed solvent of chloroform: methanol: 0.2% (w/v) calcium chloride aqueous solution=50:45:10 (v/v/v). The plate was immersed in 0.4% polyisobutylmethacrylic acid salt dissolved in hexane for 30 seconds. The plate was stained with Dittmer reagent in accordance with an ordinary method. A result is shown in FIG. 14. According to this result, the bands corresponding to GGPL-I and GGPL-III were found only in the respective species of *Mycoplasma fementans*, and the bands were not found in other mycoplasmal species. According to this fact, it has been concluded that GGPL-I and GGPL-III are glycoglycerophospholipids characteristic of *Mycoplasma fementans*.

EXAMPLE 2

Preparation of Anti-Mycoplasmal Glycolipid Polyclonal Antibody

Monophosphate lipid A (50 µg, produced by Ribi ImmunoChem Research) and complete adjuvant (50 µg, produced by nacalai tesque) were added to the lipid extract (50 mg) of *Mycoplasma fementans* obtained as described above, to which mineral oil (250 µl) was further added, followed by grinding at 400 rpm for 2 minutes. Further, PBS containing 0.1% (v/v) Tween 80 (250 µl) was added thereto, followed by grinding at 400 rpm for 2 minutes to obtain an emulsion (0.5 ml) containing the lipid extract.

The emulsion prepared by the foregoing method was subcutaneously injected to 7-weeks-old female BALB/c mice in an amount of 0.5 ml per one individual. Two weeks and three weeks after the priming immunization, the emulsion containing the lipid extract prepared by the foregoing method was intraperitoneally injected in an amount of 0.5 ml per one individual.

A serum was separated from blood of the mice immunized as described above, in accordance with an ordinary method. The serum was used to perform immunostaining as follows. A lipid fraction was extracted from GGPL-positive MT-4 cells in accordance with a known method (Bligh and Dyer, *Can. J. Biochem. Physiol.*, 37, 911–917 (1959)). The extract of the lipid fraction was applied to a high-performance thin layer chromatography (HPTLC) plate (produced by Merck), and developed with a mixed solvent of chloroform: methanol: 0.2% (w/v) calcium chloride aqueous solution= 50:45:10 (v/v/v). The plate was immersed in 0.4% polyisobutylmethacrylic acid salt dissolved in hexane for 30 seconds, and then dried in air.

The foregoing serum or a serum of a non-immunized mouse was added as a primary antibody to the HPTLC plate, followed by incubation at 4° C. overnight. The HPTLC plate was washed with PBS. After that, a peroxidase-labeled anti-rabbit IgG antibody (produced by Cappel) was added as a secondary antibody to the HPTLC plate, followed by incubation at room temperature for 4 hours. The HPTLC plate was washed with pure water. After that, bands of antigens were detected by using a peroxidase color development kit (KONICA Immunostaining HRPKit, produced by Konica). A result is shown in FIG. 15. According to this result, it was confirmed that the foregoing serum contained a polyclonal antibody against GGPL-I and GGPL-III.

EXAMPLE 3

Preparation of Anti-GGPL-III Monoclonal Antibody
(1) Preparation of Hybridoma

An emulsion containing the lipid extract of *Mycoplasma fementans* was subcutaneously injected to 7-weeks-old female BALB/c mice in an amount of 0.5 ml per one individual in the same manner as described in Example 2. Two weeks and three weeks after the priming immunization, the emulsion containing the lipid extract prepared by the foregoing method was intraperitoneally injected in an amount of 0.5 ml per one individual.

Four days after the final immunization, spleens were excised from the mice, and a cell-floating suspension was prepared by using RPMI 1640 medium. The spleen cells ($2\times10^8$ cells) were mixed with mouse myeloma SP2/0 cells at the logarithmic growth phase (azaguanine-resistant, IgG-non-secretable; ATCC CRL -1581, $2\times10^7$ cells), followed by centrifugation to obtain a residual precipitate to which 45% polyethylene glycol (PEG-4000, produced by Wako Pure Chemical, 1 ml) was added over 1 minute with mild shaking, followed by incubation for 2 minutes at 37° C. with mild shaking. RPMI 1640 medium (1 ml) was added thereto over 1 minute, followed by mild shaking. The same medium (1 ml) was added thereto over 1 minute, followed by mild shaking. After that, the same medium (8 ml) was further added thereto over 3 minutes.

After centrifuging the mixed cell suspension, the cells were floated in RPMI 1640 medium (50 ml) containing 10% fetal calf serum (FCS). The suspension was dispensed and poured into wells of four 96-well microplates in an amount of 100 µl per one well. The cells were cultured in a carbon dioxide gas incubator (5% carbon dioxide gas, 37° C.). After 24 hours, the medium was exchanged to HAT medium (10% (v/v) FCS medium containing hypoxanthine, aminopterin, and thymidine), and the cells were continuously cultured in a carbon dioxide gas incubator (5% carbon dioxide gas, 37° C.). Four days after the start of cultivation in the HAT medium, fresh HAT medium was added in an amount of 100 µl per one well. Seven days after the start of cultivation in the HAT medium, the medium was exchanged to HT medium (prepared by removing aminopterin from HAT medium). On the day following the exchange, the medium was exchanged to RPMI 1640 medium containing 10% (v/v) FCS, and then the presence or absence of colony formation was checked.

(2) Selection of Antibody-producing Hybridoma

The lipid fraction of *Mycoplasma fementans* (20 µg) was dissolved in 10 ml of ethanol to prepare a solution which was added to wells of 96-well microplate in an amount of 50 µl per one well, followed by being dried for 30 minutes with a dryer. PBS containing 1% (w/v) bovine serum albumin (BSA) was added thereto in an amount of 100 µl per one well, followed by being left to stand at room temperature for 1 hour. The wells were washed five times with a solution of 0.3 M sucrose in an amount of 100 µl per one well. After that, culture supernatants obtained from the cultures described above were added to the respective wells in an amount of 100 µl per one well, followed by shaking at room temperature for 60 minutes. The respective wells were washed with a solution of 0.05% Tween 20. After that, a peroxidase-labeled anti-mouse IgG antibody (produced by Cappel) diluted 500 times with PBS was added to the wells in an amount of 50 µl per one well, followed by shaking at room temperature for 60 minutes.

The respective wells were washed with a solution of 0.05% Tween 20. After that, a citrate buffer containing 10 mg of ortho-phenylenediamine and 50 µl of 30% (v/v) hydrogen peroxide aqueous solution per 10 ml of the buffer was added to the wells in an amount of 100 µl per one well, followed by incubation at room temperature for 15 minutes. Sulfuric acid (0.5 M) was added to the wells in an amount of 100 µl per one well to stop the enzyme reaction of peroxidase, and then the absorbance at 490 nm was measured by using a microplate reader.

Antibody-producing hybridomas were subjected to repeated cloning in accordance with the limiting dilution method. Primary screening was performed by means of ELISA based on the use of the antigen of the lipid fraction of *Mycoplasma fementans*. Colonies positive in ELISA were further subjected to secondary screening by means of immunostaining for the lipid fraction of *Mycoplasma fementans* on HPTLC. Thus a hybridoma strain, i.e., MF-III-1 strain was obtained, which produced a monoclonal antibody having reaction specificity to GGPL-III. This strain was deposited in National Institute of Bioscience and Human Technology of Agency of Industrial Science and Technology of Ministry of International Trade and Industry under a deposition number of FERM P-14324, transferred to international deposition based on the Budapest Treaty on May 26, 1995, and awarded a deposition number of FERM BP-5115.
(3) Preparation of Monoclonal Antibody The monoclonal antibody against GGPL-III was obtained by culturing the MF-III-1 strain in RPMI 1640 medium containing 10% (v/v) FCS, and recovering its culture supernatant.

EXAMPLE 4

Evaluation of Monoclonal Antibody by Immunostaining

Immunostaining was performed as described below by using the obtained anti-GGPL-III monoclonal antibody. Lipid fractions of various species of mycoplasmas (*Mycoplasma fementans* GGPL strain, *Mycoplasma fermentans* incognitus (ATCC 53949), *Mycoplasma fermentans* PG18 strain, *Mycoplasma fementans* F17 strain, *Mycoplasma fementans* F1 strain, *Mycoplasma fermentans* F7 strain, *Mycoplasma arthritidis*, and *Mycoplasma hominis* (ATCC 15488)) were extracted in accordance with a known method (Bligh and Dyer, *Can. J. Biochem. Physiol.*, 37, 911–917 (1959)). The extracts of the lipid fractions were applied to a high-performance thin layer chromatography (HPTLC) plate (produced by Merck), and developed with a mixed solvent of chloroform: methanol: 0.2% (w/v) calcium chloride aqueous solution=50:45:10 (v/v/v).

The plate was immersed in 0.4% (w/v) polyisobutyl-methacrylic acid salt dissolved in hexane for 30 seconds, and then dried in air. The anti-GGPL -III monoclonal antibody described above was added as a primary antibody to the HPTLC plate, followed by incubation at 4° C. overnight. The HPTLC plate was washed with PBS. After that, a peroxidase-labeled anti-mouse IgG antibody (produced by Cappel) was added as a secondary antibody to the HPTLC plate, followed by incubation at room temperature for 4 hours. The HPTLC plate was washed with pure water. After that, bands of the antigen was detected by using a peroxidase color development kit (KONICA Immunostaining HRPKit, produced by Konica). A result is shown in FIG. 16.

According to this result, it is clear that the monoclonal antibody of the present invention specifically binds to the glycoglycerophospholipid of *Mycoplasma fementans*, and does not bind to phospholipids and glycolipids of *Mycoplasma arthritidis* and *Mycoplasma hominis*. As for the bands stained on HPTLC with Dittmer reagent and the orcinol reagent, the band of GGPL-I and the bands identified to be GM2, GM1a, GD1a, phosphatidylcholine, and sphingomyelin were not found in the immunostaining. Thus the monoclonal antibody of the present invention specifically bound to only GGPL-III.

Next, MT-4 cells infected with *Mycoplasma fermentans* were immunostained with the anti-GGPL-III monoclonal antibody as a primary antibody, and a fluorescein isothiocyanate (FITC)-labeled anti-mouse IgG antibody as a secondary antibody, followed by observation with a fluorescent microscope. A result is shown in FIG. 17.

According to this result, it is clear that *MycoPlasma fermentans* can be detected by using the monoclonal antibody of the present invention.

EXAMPLE 5

Detection of GGPL-III or Substance Having Similar Antigenicity to GGPL-III in Blood of Nephritis Patient Serums were prepared from blood samples of nephritis patients and normal individuals in accordance with an ordinary method. Total lipids in the serums were extracted from the serums (each 100 µl) with a mixed solvent of chloroform: methanol (2:1, 1:1, and 1:2 (V/V), each 100 µl) in accordance with a known method (Bligh and Dyer, *Can. J. Biochem. Physiol.*, 37, 911–917 (1959)). The extracting solvent was divided into three layers, of which the lowermost layer was recovered. The recovered fraction was dialyzed against water, and then lyophilized. Samples obtained as described above were applied to a high-performance thin layer chromatography (HPTLC) plate (produced by Merck), and developed with a mixed solvent of chloroform: methanol: 0.2% (W/V) calcium chloride aqueous solution (50:45:10 (V/V/V)). Purified GGPL-III was used as a standard substance, which was applied and developed on the HPTLC plate in the same manner as described above.

The plate was immersed in 0.4% (w/v) polyisobutyl-methacrylic acid salt dissolved in hexane for 30 seconds, and then dried in air. The anti-GGPL -III monoclonal antibody described above was added as a primary antibody to the HPTLC plate, followed by incubation at 4° C. overnight. The HPTLC plate was washed with PBS. After that, a peroxidase-labeled anti-mouse IgG antibody (produced by Cappel) was added as a secondary antibody to the HPTLC plate, followed by incubation at room temperature for 4 hours. The HPTLC plate was washed with pure water. After that, bands of the antigen was detected by using a peroxidase color development kit (KONICA Immunostaining HRPKit, produced by Konica).

The test was performed in accordance with the method as described above for 9 specimens of serums of nephritis patients and 9 specimens of serums of normal individuals. As a result, a signal was observed in the vicinity of the position of GGPL-III for 6 specimens of the 9 specimens of the nephritis patients (FIG. 18). This signal was not detected for the specimens of the normal individuals (FIG. 18). The signal, which was frequently found in nephritis patients, was different from GGPL-III judging from the position of HPTLC. However, it is assumed that the signal represents a lipid having similar antigenicity.

Alternatively, after lipids are extracted as described above, the following steps may be adopted. Namely, the lipids are lyophilized to prepare samples. Each of the samples is dissolved in a mixed solvent of chloroform: methanol: water (83:16:0.5 (V/V/V)), and applied to Iatro-beads column (equilibrated with a mixed solvent of chloroform: methanol: water (83:16:0.5 (V/V/V)) charged with Iatrobeads 6RS-8060 (produced by Iatron). Stepwise elution is performed by changing the composition of chloroform: methanol: water to obtain an eluted fraction to be applied to HPTLC.

EXAMPLE 6

Detection of Anti-GGPL-III Antibody in Serum by ELISA Method by Using Purified GGPL-III as Antigen GGPL-III (40 µg) purified in Example 1 was dissolved in 10 ml of ethanol to prepare a solution which was added to wells of 96-well microplate in an amount of 50 µl per one well, followed by being dried with a dryer for 30 minutes. PBS containing 1% (w/v) bovine serum albumin (BSA) was added in an amount of 100 µl per one well, followed by being stationarily left to stand at room temperature for 1 hour. The plate was washed five times with a solution of 0.3 M sucrose in an amount of 100 µl per one well. After that, serums prepared in accordance with an ordinary method from blood samples of normal individuals, AIDS patients, nephritis patients, and HTLV-I associated myelopathy (HAM) patients respectively were added to the wells in an amount of 100 µl per one well, followed by shaking at room temperature for 60 minutes. The respective wells were washed with a solution of 0.05% Tween 20. After that, a peroxidase-labeled anti-human IgG antibody (produced by Cappel) diluted 2,000 times with PBS was added to the wells in an amount of 50 µl per one well, followed by shaking at room temperature for 60 minutes.

The respective wells were washed with a solution of 0.05% Tween 20. After that, a citrate buffer containing 10 mg of ortho-phenylenediamine and 50 µl of 30% (v/v) hydrogen peroxide aqueous solution per 10 ml of the buffer was added to the wells in an amount of 100 µl per one well, followed by incubation at room temperature for 15 minutes. Sulfuric acid (0.5 M) was added to the wells in an amount of 100 µl per one well to stop the enzyme reaction of peroxidase, and then the absorbance at 450 nm was measured by using a microplate reader.

The absorbance at 450 nm was measured in accordance with the method described above for serums of normal individuals (46 specimens), AIDS patients (10 specimens), nephritis patients (22 specimens), and HTLV-I associated myelopathy (HAM) patients (9 specimens). An absorbance obtained from those of the normal individuals was used as a control. Serum specimens having absorbances at 450 nm larger than the normal individuals were regarded as anti-GGPL-III antibody positive. A result is shown in Table 2.

TABLE 2

| Name of disease | Positive ratio for anti-GGPL-III antibody |
| --- | --- |
| Normal individual | 1/46 (2.2%) |
| AIDS | 8/10 (80.0%) |
| Nephritis | 3/22 (13.8%) |
| HAM | 2/9 (22.2%) |

As understood from Table 2, those which were anti-GGPL-III antibody-positive in serum were 1 specimen of the 46 specimens (2.2%) for the normal individuals, 8 specimens of the 10 specimens (80.0%) for the AIDS patients, 3 specimens of the 22 specimens (13.8%) for the nephritis patients, and 2 specimens of the 9 specimens (22.2%) for the HTLV-I associated myelopathy patients respectively. Further, investigation was made by using a peroxidase-labeled anti-human IgM antibody (produced by Cappel) instead of the secondary antibody described above (peroxidase-labeled anti-human IgG antibody). As a result, the positive ratio for the anti-GGPL-III antibody in serums of nephritis patients was further increased.

INDUSTRIAL APPLICABILITY

According to the present invention, the novel glycoglycerophospholipid originating from *Mycoplasma fermentans*, i.e., GGPL-III is obtained. Further, the antibody having reaction specificity to the glycoglycerophospholipid originating from *Mycoplasma fermentans*, especially the polyclonal antibody having reaction specificity to GGPL-I and GGPL-III, and the monoclonal antibody having reaction specificity to only GGPL-III are obtained.

The use of the antibody of the present invention makes it possible to specifically detect *Mycoplasma fermentans*. It is expected to apply the antibody of the present invention to prediction of crisis of retrovirus infectious diseases such as AIDS, diagnosis of rheumatism, and diagnosis of nephritis.

Further, the antibody of the present invention has a possibility to be used for curing or preventing infectious diseases caused by viruses which highly possibly undergo complex infection of *Mycoplasma fermentans*.

What is claimed is:

1. An isolated anti-glycoglycerophospholipid antibody immunolooically reactive with a glycoglycerophospholipid comprising at least phosphocholine, glucose, fatty acid, and glycerol, the lipid being non-adsorptive to an anion exchanger having diethylaminoethyl group, and unstable against alkali, wherein the glycoalycero-phospholipid is a glycoglycerophospholipid specifically existing in *Mycoplasma fermentans*.

2. The anti-glycoglycerophospholipid antibody according to claim 1, which immunoloically reacts with both of 6'-O-phosphocholine-α-glucopyranosyl-(1'-3)-1,2-diacyl-sn-glycerol and a glycoglycerophospholipid purified from *Mycoplasma fermentans*, having the following properties:

(A) the glycozlycerophospholipid is reactive with orcinol reagent, Dittmer reagent, Dragendorff reagent and ninhydrin reagent;

(B) the glycoglycerophospholipid is degradable with alkali;

(C) the glycozylcerophospholipid is obtained as a non-adsorptive fraction upon fractionation with an anion exchanger having diethylaminoethyl group; and (D) the glycozylycerophospholipid has a molecular weight of 1048+28n measured by using a mass spectrometer, wherein n is −1, 0, 1 or 2.

3. The anti-glycoglycerophospholipid antibody according claim 1, which is a polyclonal antibody.

4. The anti-glycoglycerophospholipid antibody according to claim 1, which immunologically reacts with only a glycoglycerophospholipid purified from *Mycoplasma fermentatans*, having the following properties:

(A) the glycoglycerophospholipid is reactive with orcinol reagent, Dittmer reagent, Dragendorff reagent, and ninhydrin reagent;

(B) the glycoglycerophospholipid is deoradable with alkali;

(C) the glycoglycerophospholipid is obtained as a non-adsorptive fraction upon fractionation with an anion exchanger having diethylaminoethyl group; and (D) the glycoglycerophospholipid has a molecular weight of 1048+28n measured by using a mass spectrometer, wherein n is −1, 0, 1, or 2.

5. The anti-glycoglycerophospholipid antibody according to claim 1, which is a monoclonal antibody or a fragment thereof.

6. The anti-glycoglycerophospholipid antibody according to claim 1, which specifically recognizes *Mycoplasma fementans*, and does not recognize other species of mycoplasmas.

7. The anti-glycoglycerophospholipid antibody according to claim 6, wherein the other species of mycoplasmas are *Mycoplasma arthritidis* and *Mycoplasma hominis*.

8. The anti-glycoglycerophospholipid antibody according to claim 1, which makes no cross reaction with sialic acid-containing glycolipid (ganglioside), platelet-activating factor (1-alkyl-2-acetylglycero-3-phosphocholine) or a partially deacylated product thereof, phosphatidylcholine or a partially deacylated product thereof, and sphingomyelin.

9. A method for measuring a glycoglycerophospholipid, comprising the step of immunologically measuring the glycoglycerophospholipid having the following properties contained in a specimen, by using the anti-glycoglycerophospholipid antibody as defined in claim 1:

the glycoglycerophospholipid comprises at least phosphocholine, glucose, fatty acid, and glycerol, the lipid being non-adsorptive to an anion exchanger having diethylaminoethyl group, and unstable against alkali.

10. A method for measuring a substance, which is immunologically reactive with the isolated anti-glycoglycerophospholipid antibody of claim 1, contained in a specimen, comprising the step of immunologically measuring the substance by measuring the binding to the anti-glycoglycerophospholipid antibody.

11. A method for measuring a glycoglycerophospholipid contained in a specimen, comprising the steps of allowing a specimen solution to contact with a solid phase including the anti-glycoglycerophospholipid antibody as defined in claim 1 bound thereto so that the glycoglycerophospholipid contained in the specimen solution is bound to the antibody, separating and removing non-adsorptive components from the solid phase, subsequently allowing a glycoglycerophospholipid originating from *Mycoplasma fementans* labeled with a label substance to contact with the solid phase, making a competitive reaction between the glycoglycerophospholipid contained in the specimen solution and the labeled glycoglycerophospholipid, and detecting any one of the label substance bound to the solid phase and the label substance not bound to the solid phase.

12. A method for detecting *Mycoplasma fementans* contained in a specimen, comprising the steps of extracting a lipid fraction from the specimen, allowing the extracted lipid fraction to contact with a solid phase so that the lipid is adsorbed to the solid phase, reacting the solid phase including the lipid adsorbed thereto with the anti-glycoglycerophospholipid antibody as defined claim 1, simultaneously or subsequently making a reaction with a secondary antibody obtained by labeling an antibody against immunoglobulin of an immunized animal with a label substance, the antibody against the immunoglobulin of the immunized animal having been prepared by using an animal other than the immunized animal used to prepare the anti-glycoglycerophospholipid antibody, and detecting the label substance.

13. A method for detecting *Mycoplasma fementans*, comprising the steps of reacting the anti-glycoglycerophospholipid antibody as defined in claim 1 labeled with a label substance, with a tissue or cells of a living organism exactly or after applying a treatment for immobilizing a glycoglycerophospholipid, binding the labeled antibody to the tissue or cells of the living organism infected with *Mycoplasma fementans*, and detecting the label substance.

14. A method for detecting *Mycoplasma fementans*, comprising the steps of reacting the anti-glycoglycerophospholipid antibody as defined in claim 1 with a tissue or cells of a living organism exactly or after applying a treatment for immobilizing a glycoglycerophospholipid, simultaneously or subsequently making a reaction with a secondary antibody obtained by labeling an antibody against immunoglobulin of an immunized animal with a label substance, the antibody against the immunoglobulin of the immunized animal having been prepared by using an animal other than the immunized animal used to prepare the anti-glycoglycerophospholipid antibody, binding the labeled secondary antibody to the tissue or cells of the living organism infected with *Mycoplasma fementans*, and detecting the label substance.

15. A reagent kit for detecting *Mycoplasma fermentans* or a glycoglycerophospholipid of *Mycoplasma fermentans* contained in a specimen in accordance with an immunological method, comprising the anti-glycoglycerophospholipid antibody as defined in claim 1, and a glycoglycerophospholipid of *Mycoplasma fementans* labeled with a label substance.

16. A reagent kit for detecting *Mycoplasma fermentans* or a glycoglycerophospholipid of *Mycoplasma fermentans* contained in a specimen in accordance with an immunological method, comprising the anti-glycoglycerophospholipid antibody as defined in claim 1, and a secondary antibody obtained by labeling an antibody against immunoglobulin of an immunized animal with a label substance, the antibody against the immunoglobulin of the immunized animal being prepared by using an animal other than the immunized animal used to prepare the anti-glycoglycerophospholipid antibody.

17. A method for measuring a glycoglycerophospholipid specifically existing in *Mycoplasma fementans* in a specimen, comprising the step of immunologically measuring the glycoglycerophospholipid by using the anti-glycoglycerophospholipid antibody as defined in claim 1.

18. A method for detecting *Mycoplasma fementans*, comprising the steps of measuring a glycoglycerophospholipid contained in a specimen in accordance with the measuring method as defined in claim 17, and relating the presence or absence of the glycoglycerophospholipid or an existing amount thereof to the presence or absence of *Mycoplasma fementans* or an existing amount thereof in the specimen.

19. The method for detecting *Mycoplasma fementans* according to claim 18, wherein the glycoglycerophospholipid contained in the specimen is a lipid fraction extracted from the specimen originating from a living organism.

20. The method for detecting *Mycoplasma fementans* according to claim 19, wherein the specimen originating from the living organism is blood, serum, plasma, cerebrospinal fluid, urine, synovial fluid, or cultured cell solution.

* * * * *

UNITED STATES PATENT AND TRADEMARK OFFICE
CERTIFICATE OF CORRECTION

PATENT NO.    : 6,376,203 B1
DATED         : April 23, 2002
INVENTOR(S)   : Kazuhiro Matsuda and Naoki Yamamoto It is certified that error appears in the above-identified patent and that said Letters Patent is hereby corrected as shown below:

<u>Title page,</u>
Add:
-- [62]  Division of Application No. 08/750,677, filed as an international application No. PCT/JP95/01091 on June 2, 1995, now Patent No. 5,994,090 --

Signed and Sealed this

First Day of October, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO. : 6,376,203 B1
DATED : April 23, 2002
INVENTOR(S) : Kazuhiro Matsuda and Naoki Yamamoto It is certified that error appears in the above-identified patent and that said Letters Patent is hereby corrected as shown below:

Column 26,
Line 19, "glycoalycero-phospholipid" should be changed to -- glycoglycerophospholipid --
Line 23, "immunoloically" should be changed to -- immunologically --
Line 27, "glycozlycerophospholipid" should be changed to -- glycoglycerophospholipid --
Line 32, "glycozylcerophospholipid" should be changed to -- glycoglycerophospholipid --
Line 35, "glycozylycerophospholipid" should be changed to -- glycoglycerophospholipid --
Line 43, "*fermentatans*" should be changed to -- *fermentans* --
Line 48, "deoradable" should be changed to -- degradable --
Line 61, "*fementans*" should be changed to -- *fermentans* --

Column 27,
Lines 29, 36 and 51, "*fementans*" should be changed to -- *fermentans* --

Column 28,
Lines 1, 3, 17, 23, 37, 41, 47, 48 and 52, "*fementans*" should be changed to -- *fermentans* --

Signed and Sealed this

Sixth Day of May, 2003

JAMES E. ROGAN
*Director of the United States Patent and Trademark Office*